United States Patent [19]
Mitch et al.

[11] Patent Number: 6,124,312
[45] Date of Patent: Sep. 26, 2000

[54] HETEROCYCLIC COMPOUNDS

[75] Inventors: Charles H Mitch, Columbus; Steven J Quimby, Noblesville; Jon K Reel, Carmel; Celia A Whitesitt, Greenwood, all of Ind.

[73] Assignee: Eli Lilly and Company, Indianapolis, Ind.

[*] Notice: This patent is subject to a terminal disclaimer.

[21] Appl. No.: 09/171,806

[22] Filed: Jun. 1, 1999

Related U.S. Application Data

[63] Continuation of application No. PCT/US97/06675, Apr. 23, 1997, which is a continuation of application No. 60/016,007, Apr. 23, 1996.

[51] Int. Cl.[7] .......................... A61K 31/44; C07D 221/22
[52] U.S. Cl. .......................... 514/295; 514/362; 548/135; 546/97
[58] Field of Search ................. 548/135; 546/84, 546/85, 97, 260.7; 514/362, 879, 295

[56] References Cited

U.S. PATENT DOCUMENTS

| | | | |
|---|---|---|---|
| 5,605,908 | 2/1997 | Merritt et al. | 514/305 |
| 5,646,289 | 7/1997 | Alt et al. | 548/110 |

FOREIGN PATENT DOCUMENTS

| | | | |
|---|---|---|---|
| 0 709 381 A1 | 5/1996 | European Pat. Off. | 285/10 |

*Primary Examiner*—Amelia Owens
*Attorney, Agent, or Firm*—David M. Stemerick; Arleen Palmberg; MaCharri Vorndran-Jones

[57] ABSTRACT

The present invention provides heterocyclic 2-aza-bicyclo[2.2.1]heptane compounds which are useful for modulating a muscarinic ptor.

20 Claims, No Drawings

HETEROCYCLIC COMPOUNDS

This application is a 371 of PCT/US97/06675 filed Apr. 23, 1997, and a provision of Ser. No. 60/016007 filed Apr. 23, 1996.

The present invention relates to therapeutically active 2-azabicyclo-2.2.1 compounds having surprising potency and favorable side effect profile. The novel compounds are useful as stimulants of the cognitive function of the forebrain and hippocampus of mammals.

Due to the generally improved health situation in the western world, elderly-related diseases are much more common now than in the past and are likely to be even more common in the future.

One of the elderly-related symptoms is a reduction of the cognitive functions. This symptom is especially pronounced in the pathophysiological disease known as Alzheimer's disease. This disease is combined with, and also most likely caused by, an up to 90% degeneration of the muscarinic cholinergic neurons in nucleus basalis, which is part of substantia innominata. These neurons project to the prefrontal cortex and hippocampus and have a general stimulatory effect on the cognitive functions of the forebrain as well as of hippocampus, namely learning, association, consolidation, and recognition.

It is a characteristic of Alzheimer's disease that although the cholinergic neurons degenerate, the postsynaptic muscarinic receptors in the forebrain and hippocampus still exist. Therefore, muscarinic cholinergic agonists are useful in the treatment of Alzheimer's disease, in halting its progression, and in improving the cognitive functions of elderly people.

Compounds active at a muscarinic cholinergic receptor are also useful analgesic agents and therefore are useful in the treatment of severely painful conditions.

Furthermore, muscarinic cholinergic receptor active compounds are useful in the treatment of glaucoma, psychosis, anxiety, mania, bipolar disorder, schizophrenia or schizophreniform conditions, depression, sleeping disorders, epilepsy, cerebral ischemia, and gastrointestinal motility disorders.

Therefore, new compounds having muscarinic cholinergic activity are desired. Some muscarinic cholinergic receptor active compounds are associated with side effects attributed to undesired modulation of the muscarinic cholinergic receptors, for example, such undesired modulation may cause excessive salivation and gastrointestinal upset. Thus, the most desired muscarinic cholinergic compounds shall have high potency and at the same time a favorable side effect profile, including a low incidence of excessive salivation.

The presently claimed compounds are surprisingly potent and also provide a favorable side effect profile. The observed characteristics of these compounds suggest that they will be especially desirable muscarinic receptor active compounds which can be useful pharmaceutically active agents.

This invention provides compounds of the formula

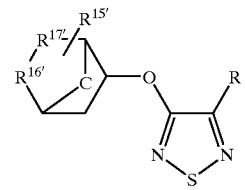

R is selected from the group consisting of —$OR^4$, —$SR^4$, and $SO_2R^4$;

$R^4$ is selected from the group consisting of $C_{1-15}$-alkyl, $C_{2-15}$-alkenyl, $C_{2-15}$-alkynyl, fused aromatic, and 5-membered heterocycle; each of which is optionally substituted with one or more independently selected from the group consisting of $C_3$–$C_8$ cycloalkyl, halogen(s), —$CF_3$, —CN, $C_{1-4}$ alkoxy, fused aromatic, 5-membered heterocycle, phenyl and phenoxy wherein phenyl, fused aromatic, and phenoxy is optionally substituted with one or more independently selected from the group consisting of halogen, —CN, $C_{1-4}$-alkyl, $C_{1-4}$-alkoxy, —$OCF_3$, —$CF_3$, —$CONH_2$ and —$CSNH_2$;

$R^{16'}$ is carbon or nitrogen;
$R^{17'}$ is carbon or nitrogen;
provided that one, and only one, of $R^{16'}$ and $R^{17'}$ must be nitrogen and when $R^{16'}$ is nitrogen then $R^{17'}$ is carbon and when $R^{17'}$ is nitrogen then $R^{16'}$ is carbon;

$R^{15'}$ is selected from the group consisting of hydrogen, $C_{1-4}$ alkyl, $C_{1-4}$ alkenyl, $C_{1-4}$ alkynyl, —$C(O)OR^{20'}$ and $C_3$–$C_8$ cycloalkyl;

$R^{20'}$ is $C_1$–$C_6$ alkyl; or a pharmaceutically acceptable salt or solvate thereof.

It is an object of the invention to provide new muscarinic cholinergic compounds having surprising potency and a favorable side effect profile.

It is to be understood that the invention extends to each of the stereoisomeric forms of the compounds of the present invention as well as the pure diastereomeric, pure enantiomeric, and racemic forms of the compounds of this invention.

As used herein the term "treating" includes prophylaxis of a physical and/or mental condition or amelioration or elimination of the developed physical and/or mental condition once it has been established or alleviation of the characteristic symptoms of such condition.

As used herein the phrase "interacting with a muscarinic cholinergic receptor" shall include compounds which block muscarinic cholinergic receptors or modulate such receptors. The phrase shall include the effect observed when compounds act as agonists, partial agonists and/or antagonists at a muscarinic cholinergic receptor.

As used herein, the $R^{15'}$ substituent may be at any position in the azacyclic ring system, including, but not limited to at the bridgehead position and on the nitrogen atom of the ring system.

As used herein, the term "halogen" means Cl, Br, F, and I. Especially preferred halogens include Cl, Br, and I.

As used herein the phrase "one or more selected from" shall more preferredly refer to from 1–3 substituents. The term shall further preferredly refer to from 1–2 substituents.

The terms "$C_1$–$C_{n'}$ alkyl" wherein n' can be from 2 through 15, as used herein, represent a branched or linear alkyl group having from one to the specified number of carbon atoms. Typical $C_1$–$C_6$ alkyl groups include, but are not limited to, methyl, ethyl, n-propyl, iso-propyl, butyl, iso-butyl, sec-butyl, tert-butyl, pentyl, hexyl and the like.

The terms "$C_2$–$C_{n'}$ alkenyl" wherein n' can be from 3 through 10, as used herein, represents an olefinically unsaturated branched or linear group having from 2 to the specified number of carbon atoms and at least one double bond. Examples of such groups include, but are not limited to, 1-propenyl, 2-propenyl (—$CH_2$—CH=$CH_2$), 1,3-butadienyl, (—CH=CHCH=$CH_2$), 1-butenyl (—CH=CHCH$_2$CH$_3$), hexenyl, pentenyl, and the like.

The term "$C_2$–$C_{n''}$ alkynyl" wherein n" can be from 3 to 15, refers to an unsaturated branched or linear group having from 2 to n" carbon atoms and at least one triple bond. Examples of such groups include, but are not limited to, 1-propynyl, 2-propynyl, 1-butynyl, 2-butynyl, 1-pentynyl, and the like.

The term "$C_3$–$C_n$ cycloalkyl" wherein n=4–8, represents cyclopropyl, cyclobutyl, cyclopentyl, cyclohexyl, cycloheptyl, and cyclooctyl.

The term "$C_5$–$C_8$ cycloalkenyl" represents an olefinically unsaturated ring having five to eight carbon atoms. Such groups include, but are not limited to, cyclohexyl-1,3-dienyl, cyclohexenyl, cyclopentenyl, cycloheptenyl, cyclooctenyl, cyclohexyl-1,4-dienyl, cycloheptyl-1,4-dienyl, cyclooctyl-1,3,5-trienyl and the like.

As used herein the term "carboxy" refers to a substituent having the common meaning understood by the skilled artisan, wherein the point of attachment may be through the carbon or oxygen atom of the group.

As used herein, the term "optionally substituted" refers to from zero to four substituents, wherein the substituents are each independently selected. More preferredly, the term refers to from zero to three independently selected substituents. Each of the independently selected substituents may be the same or different than other substituents.

As used herein the term "aryl" means an organic radical derived from an aromatic hydrocarbon by the removal of one atom; e.g., phenyl or naphthyl. Most preferably, aryl refers to $C_6$–$C_{10}$ aryl, wherein the aryl ring system, including any alkyl substitutions, comprises from 6 to 10 carbon atoms; e.g., phenyl, 3,3-dimethylphenyl, naphthyl, and the like. The aryl radical may be substituted by one or two $C_1$–$C_6$ straight or branched alkyl. The term "aryl($C_1$–$C_3$) alkyl" refers to any aryl group which is attached to the parent moiety via the alkyl group.

The phrase "5-membered heterocycle" includes, but is not limited to, 5-membered heterocycles having one hetero atom (e.g. thiophenes, pyrroles, furans); 5-membered heterocycles having two heteroatoms in 1,2 or 1,3 positions (e.g. oxazoles, pyrazoles, imidazoles, thiazoles, purines); 5-membered heterocycles having three heteroatoms (e.g. triazoles, thiadiazoles).

The term "heterocyclic group" refers to a $C_3$–$C_8$ cycloalkyl group containing from one to three heteroatoms wherein the heteroatoms are selected from the group consisting of oxygen, sulfur, and nitrogen.

The term "fused aromatic" refers to a $C_3$–$C_8$ cycloalkyl group or $C_3$–$C_8$ heterocyclic group fused to an aryl group, as defined supra. An especially preferred aryl is a phenyl group fused to the hetercyclic group. The fused aromatic may be substituted at any position on the substituent including on the heterocyclic group and on the aromatic group.

Examples of pharmaceutically acceptable salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts, and include the pharmaceutically acceptable salts listed in *Journal of Pharmaceutical Science,* 66, 2 (1977) which are known to the skilled artisan. The compounds of this invention may form solvates with standard low molecular weight solvents using methods known to the skilled artisan.

The compounds of this invention can be prepared using the chemical processes illustrated in Scheme I' and Scheme I. The starting materials for the illustrated process are commercially available or may be prepared using methods known to the skilled artisan.

SCHEME I'
Synthesis Scheme for 2-Aza compounds

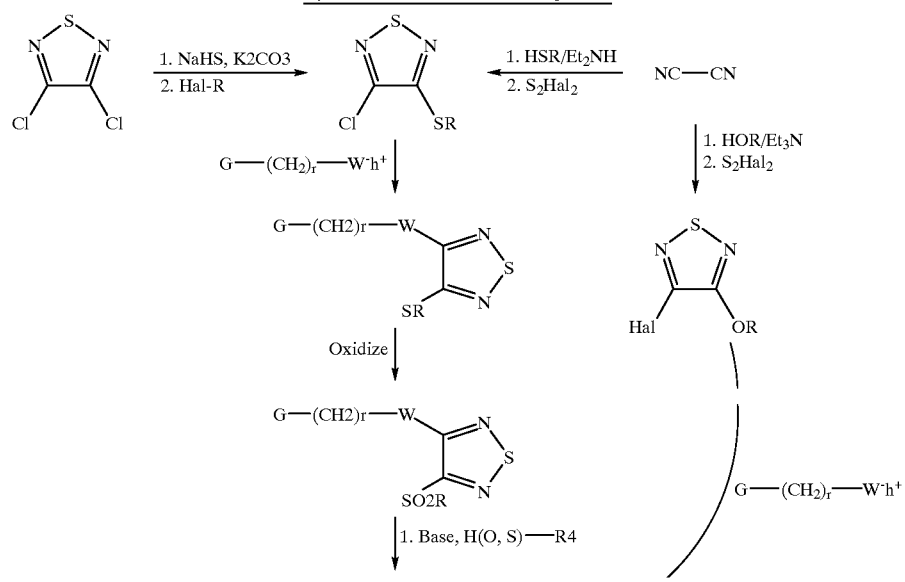

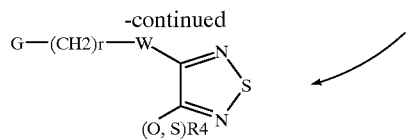

As used in Scheme I, R, h+, and G are as defined supra. As used in Scheme I, the term "Hal" refers to Cl, Br, and $R^9SO_2$. Preferred oxidizing agents for the process of Scheme I include oxone and sodium periodate. Oxone is an especially preferred oxidizing agent for the process of Scheme I. Compounds of Formula 3, as illustrated in Scheme I wherein the OR group is replaced by an $R^4$ group, can be prepared using methods well known in the art. See for example, U.S. Pat. No. 5,043,345.

Further, compounds of Formula I may be prepared using the process illustrated in the following Scheme II As used in Scheme II, Q may be N, O or S; $R^{24}$ is selected from the group consisting of hydrogen, $R^4$, $R^5$, $R^6$, and $R^7$; $R^{25}$ is selected from the group consisting of $SOR^4$ and $SO_2R^4$; all other meanings are as defined supra.

Additional compounds of Formula I may be prepared using the process illustrated by Scheme III.

Scheme III

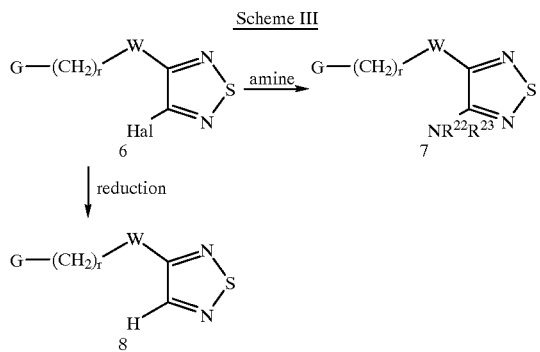

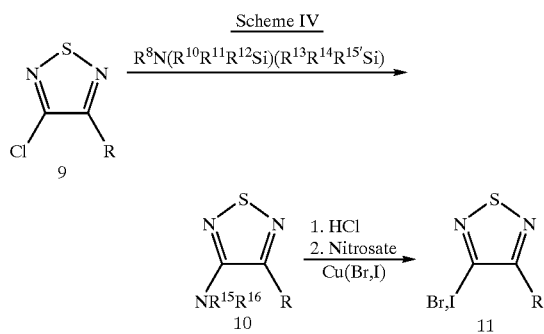

As used in Scheme III, Hal, W, r, and G are as defined supra. As used in Scheme III, $R^{22}$ and $R^{23}$ are independently selected from the group consisting of hydrogen, $R^6$ and $R^7$.

Certain intermediates of the present invention may be prepared using the process illustrated in Scheme IV.

As used in Scheme IV, $R^8$, Si, $R^{10}$, $R^{11}$, $R^{12}$, $R^{13}$, $R^{14}$, $R^{15'}$, $R^{15}$ and $R^{16}$ are as defined supra. For example, $R^8N$ [($R^{10}R^{11}R^{12}Si$) ($R^{13}R^{14}R^{15'}Si$)] may be, but is not limited to lithium bis(tri-2-propylsilyl)amide, sodium bis(trimethylsilyl)amide, potassium bis(trimethylsilyl)amide, lithium bis(tri-2-propylsilyl)amide, sodium bis(ethyldimethylsilyl)amide, potassium bis(1-propylethylmethylsilyl)amide, lithium bis(tri-phenylsilyl)amide, sodium bis(tri-phenylmethylsilyl)amide, potassium bis(2-butyl-2-propylmethylsilyl)amide, lithium (tri-2-propylsilyl)(2-butyldiethylsilyl)amide, sodium (trimethylsilyl)(triphenylsilyl)amide, potassium (dimethyl phenylsilyl)(ethyldimethylsilyl)amide, and the like. Most preferably, $R^{15}$ and $R^{16}$ are each hydrogen when the process of Scheme III is used for preparing a compound of 11 from a compound of 10. The intermediate 10 may be nitrosated using standard nitrosating procedures. A preferred nitrosating agent is isoamyl nitrite; however, other known nitrosating agents are appropriate. As used in Scheme III, the term "Cu(Br,I)" refers to copper (I) bromide, copper (II) bromide, or copper (I) iodide. The artisan will recognize that the copper (I) bromide, copper (II) bromide, or copper (I) iodide reagent shall determine the substitution on the product of the process illustrated in Scheme III.

Certain compounds of this invention may more preferably be prepared by a process using a hydroxyalkylamine (G-OH) wherein G has the meaning defined supra. in the presence of a phosphorus(III) compound and a diester of azodicarboxylate to give the 1,2,5-thiadiazoyloxyalkylamine as illustrated by Scheme V.

Scheme V

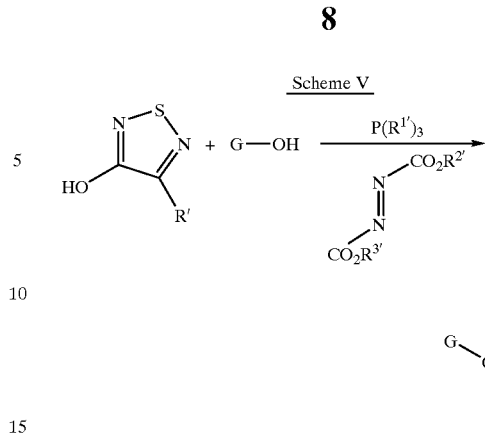

The G group is 2-aza-bicyclo[2.2.1]heptane. The R' is selected from the group consisting of —$OR^4$ and —$SR^4$ $R^4$ is selected from the group consisting of $C_{1-15}$-alkyl, $C_{2-15}$-alkenyl, $C_{2-15}$-alkynyl and 5-membered heterocycle, each of which is optionally substituted with one or more independently selected from the group consisting of halogen (s), —$CF_3$, —CN, Y, phenyl and phenoxy wherein phenyl or phenoxy is optionally substituted with one or more independently selected from the group consisting of halogen, —CN, $C_{1-4}$-alkyl, $C_{1-4}$-alkoxy, —$OCF_3$, or —$CF_3$; or R' is phenyl or benzyloxycarbonyl, each of which is optionally substituted with one or more independently selected from the group consisting of halogen, —CN, $C_{1-4}$-alkyl, $C_{1-4}$-alkoxy, —$OCF_3$, and —$CF_3$; or R' selected from the group consisting of —$OR^5Y$, —$SR^5Y$, $OR^5$—Z—Y, —$SR^5ZY$, —O—$R^5$—Z—$R^4$ and —S—$R^5$—Z—$R^4$;

Z is oxygen or sulphur;

$R^5$ is selected from the group consisting of $C_{1-15}$-alkyl, $C_{2-15}$-alkenyl, and $C_{2-15}$-alkynyl;

Y is a 5-membered heterocyclic group;

$R^{1'}$ is selected from the group consisting of phenyl, $C_{1-15}$-alkyl, $C_{2-5}$-alkenyl, $C_{2-5}$-alkynyl and $(NR^{2'})_3$;

$R^{2'}$ and $R^{3'}$ are independently selected from the group consisting of hydrogen, $C_{1-5}$-alkyl, $C_{2-5}$-alkenyl, $C_{2-5}$-alkynyl, and C1-5-alkyl substituted with one or more selected from the group consisting of halogen and phenyl;

W is oxygen or sulphur;

$R^6$, and $R^7$ independently are $C_{1-6}$-alkyl; or $R^6$ and $R^7$ together with the nitrogen atom optionally form a 4- to 6-member ring;

$R^1$ and $R^2$ are independently selected from hydrogen, $C_{1-15}$-alkyl, $C_{2-5}$-alkenyl, $C_{2-5}$-alkynyl, $C_{1-10}$-alkoxy, and $C_{1-5}$-alkyl substituted with one or more independently selected from the group consisting of —$COR^{6'}$, halogen, and phenyl;

$R^{6'}$ is hydrogen or $C_1$–$C_3$ alkyl;

$R^3$ is selected from the group consisting of $C_{1-5}$-alkyl, $C_{2-5}$-alkenyl and $C_{2-5}$-alkynyl;

n is 0, 1 or 2;

m is 0, 1 or 2;

p is 0, 1 or 2;

q is 1 or 2;

r is 0, 1 or 2;

‒‒‒‒‒‒‒‒ is a single or double bond.

Preferred $R^{1'}$ groups include phenyl, $C_{1-15}$-alkyl, and $(NR^{2'})_3$. The process of Scheme IV is particularly advantageous because the process provides a method for inverting the stereochemistry at the carbon bearing the hydroxyl group in G.

Another new process illustrated by Scheme VI, involves the sequential reaction of 3,4-dihydroxy-1,2,5-thiadiazole with G-OH wherein G is defined as defined supra. in the presence of a phosphorous(III) compounds and a diester of azodicarboxylate to give an unisolated hydroxy-1,2,5-thiadiazole ether I" followed by reaction of I" with R⁴OH where R⁴ is defined as supra. with phosphorous(III) compounds and a diester of azodicarboxylate to give the diethers of 3,4-dihydroxy-1,2,5-thiadiazole which are useful as muscarinic agonists and antagonists. (See, *Org. Prep. & Procedures* 1969, 1, 255–258) The substituents illustrated in Scheme VI are as defined supra.

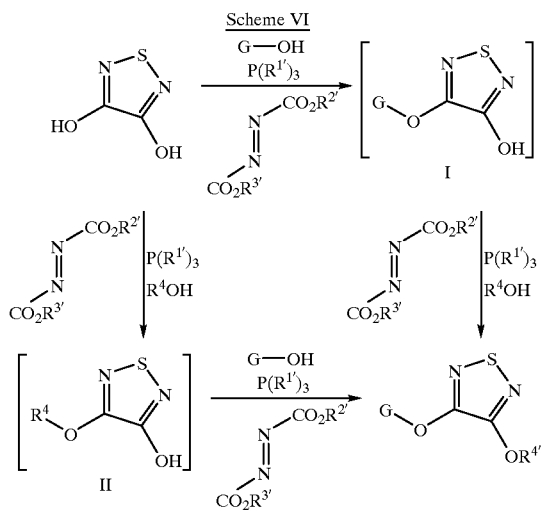

Alternatively, the order of addition of the alcohols may be reversed as shown above to give unisolated hydroxy-1,2,5-thiadiazole ether II which is subsequently converted to the same final muscarinic active compound.

The process illustrated by Scheme VII encompases the reaction of a phenol or hydroxyheteroaryl compound with compound III in the presence of a phosphorus(III) compound and a diester of azodicarboxylate to give compound IV.

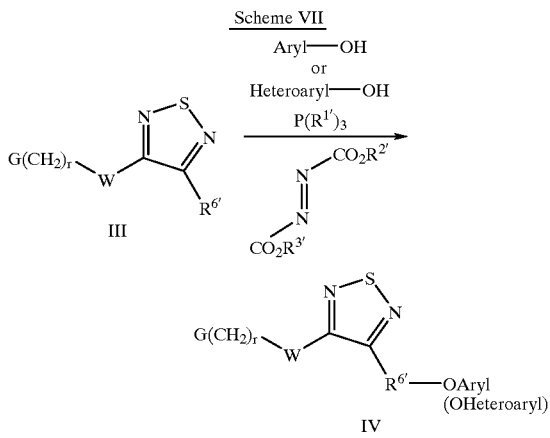

In compound III, $G(CH_2)_rW$ is 2-Aza-bicyclo[2.2.1] heptane and $R^{6'}$ is selected from the group consisting of $R^7$, —$OR^7$, —$SR^7$, —$SOR^7$, —$SO_2R^7$, $C_{3-10}$-cycloalkyl, $C_{4-12}$-(cycloalkylalkyl), —Z—$C_{3-10}$-cycloalkyl and —Z—$C_{4-12}$-(cycloalkylalkyl);

$R^7$ is $C_{1-15}$-alkyl, $C_{2-15}$-alkenyl, $C_{2-15}$-alkynyl, each of which is optionally substituted with one or more independently selected from the group consisting of halogen(s), —$CF_3$, —CN, Y, phenyl and phenoxy; wherein phenyl or phenoxy is optionally substituted with one or more selected from the group consisting of halogen, —CN, $C_{1-4}$-alkyl, $C_{1-4}$-alkoxy, —$OCF_3$, and —$CF_3$;

provided that at least one alkyl atom of $R^{6'}$ is substituted with a hydroxyl group or $R^{6'}$ is a substituent selected from the group consisting of —$OR^8Y$, —$SR^8Y$, $OR^8$—Z—Y, —$SR^8ZY$, —O—$R^8$—Z—$R^7$ and —S—$R^8$—Z—$R^7$ wherein each —$OR^8Y$, —$SR^8Y$, $OR^8$—Z—Y, —$SR^8ZY$, —O—$R^8$—Z—$R^7$ and —S—$R^8$—Z—$R^7$ is substituted with a alkylhydroxyl;

Y is a 5 or 6 membered heterocyclic group;

Z is oxygen or sulphur;

$R^8$ is $C_{1-15}$-alkyl, $C_{2-15}$-alkenyl, $C_{2-15}$-alkynyl; aryl and heteroaryl is optionally substituted with one or more independently selected from the group consisting of halogen, —CN, $C_{1-4}$-alkyl, $C_{1-4}$-alkoxy, $C_{1-4}$-alkylthio, $C_{1-4}$-alkylsulfone, $C_{1-4}$-alkylsulfoxide, —$OCF_3$, $NO_2$, $N(R^7)_2$, and —$CF_3$; heteroaryl group is a 5 or 6 membered heterocycle containing one to four N, O, or S atoms or a combination thereof.

Another process of this invention, illustrated by Scheme VIII, is the synthesis of 3-hydroxy-4-alkylthio-1,2,5-thiadiazoles by treating 3-halo-4-alkylthio-1,2,5-thiadiazoles with aqueous alkaline metal hydroxides in the presence or absence of a dipolar aprotic solvent. In this scheme, Hal has the meanings defined supra. and M is an alkali metal, W is O or S.

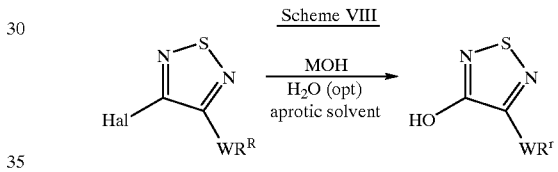

$R^R$ is hydrogen, $R^4$, $C_{3-10}$-cycloalkyl, $C_{4-12}$-(cycloalkylalkyl), $R^4$—Z—$C_{3-10}$-cycloalkyl and $R^4$—Z—$C_{4-12}$-(cycloalkylalkyl); W is oxygen or sulfur;

$R^4$ is selected from the group consisting of $C_{1-15}$-alkyl, $C_{2-15}$-alkenyl, and $C_{2-15}$-alkynyl, each of which is optionally substituted with one or more independently selected from the group consisting of halogen(s), —$CF_3$, Y, phenyl and phenoxy; wherein phenyl or phenoxy is optionally substituted with one or more selected from the group consisting of halogen, $C_{1-4}$-alkyl, $C_{1-4}$-alkoxy, and —$CF_3$; or $R^R$ is phenyl or benzyloxycarbonyl, each of which is optionally substituted with one or more selected from the group consisting of halogen, $C_{1-4}$-alkyl, $C_{1-4}$-alkoxy, and —$CF_3$; or $R^R$ is $R^4$—$OR^5Y$, $R^4$—$SR^5Y$, $R^4$—$OR^5$—Z—Y, $R^4$—$SR^5ZY$, $R^4$—O—$R^5$—Z—$R^4$ or $R^4$—S—$R^5$—Z—;

Z is oxygen or sulphur;

$R^5$ is selected from the group consisting of $C_{1-15}$-alkyl, $C_{2-15}$-alkenyl, and $C_{2-15}$-alkynyl;

Y is a 5 or 6 membered heterocyclic group; and $R^6$, and $R^7$ independently are hydrogen, $C_{1-6}$-alkyl, or $R^6$ and $R^7$ together with the nitrogen atom optionally form a 4- to 6-member ring;

$R^1$ and $R^2$ independently are hydrogen, $C_{1-15}$-alkyl, $C_{2-5}$-alkenyl, $C_{2-5}$-alkynyl, $C_{1-10}$-alkoxy, $C_{1-5}$-alkyl substituted with —OH, —$COR^{6'}$, $CH_2$—OH, halogen, —$NH_2$, carboxy, or phenyl;

$R^{6'}$ is hydrogen or $C_1$–$C_3$ alkyl;

W is O or S;

Hal is selected from Cl, Br, F, I, and if W is O then Hal may be $SO_2R^{4'}$;

$R^{4'}$ is $C_1$–$C_3$ alkyl or phenyl.

The compounds (11) are useful intermediates for the preparation of 1,2,5-thiadiazole compounds. The artisan will recognize that the intermediates 11 are useful for preparing 1,2,5-thiadiazole compounds as illustrated by the processes of Schemes I, II, and III.

When the G substituent contains a secondary nitrogen protected by a protecting group, the protecting group may be removed using standard methods known to the skilled artisan. An especially preferred protecting group is carbamate. One particularly useful reference concerning protecting groups is Greene, *Protecting Groups in Organic Synthesis*, (John Wiley & Sons, New York, 1981).

The concentration of the reactants is not critical. The art worker can alter the concentration of the reactants to achieve the desired rate of reaction and product yield.

The length of time for carrying out the processes described are not critical. As is always the case in chemistry, the rate of the reaction depends on a variety of factors, such as the temperature and the exact compound which is to be prepared. The course of the reaction may be followed using methods such as thin layer chromatography (TLC), high performance liquid chromatography (HPLC), gas chromatography (GC) and nuclear magnetic resonance spectroscopy (NMR) to detect the degree of completion of the reaction. The operator may obtain maximum yields using the process by extending the reaction time. Alternatively, the operator may wish to obtain maximum throughput by cutting off the reaction at the point at which it reaches an economical degree of completion.

When the product of a step in the following process is an oil, it may be isolated by standard methods. Such methods include distillation, flash chromatography, HPLC and the like.

As used herein the term "malfunctioning of the muscarinic cholinergic system" shall have the meaning accepted by the skilled artisan. For example the term shall refer to, but is not in any way limited to, conditions such as glaucoma, psychosis, schizophrenia or schizophreniform conditions, depression, sleeping disorders, epilepsy, and gastrointestinal motility disorders. Other such conditions include Alzheimer's Disease and incontinence.

The pharmacological properties of the compounds of the invention can be illustrated by determining their capability to inhibit the specific binding of $^3$H-Oxotremorine-M ($^3$H-Oxo). Birdsdall N. J. M., Hulme E. C., and Burgen A. S. V. (1980). "The Character of Muscarinic Receptors in Different Regions of the Rat Brain". Proc. Roy. Soc. London (Series B) 207,1.

$^3$H-Oxo labels muscarinic receptor in the CNS (with a preference for agonist domains of the receptors). Three different sites are labeled by $^3$H-Oxo. These sites have affinity of 1.8, 20 and 3000 nM, respectively. Using the present experimental conditions only the high and medium affinity sites are determined.

The inhibitory effects of compounds on $^3$H-oxo binding reflects the affinity for muscarinic acetylcholine receptors.

All preparations are performed at 0–4° C. unless otherwise indicated. Fresh cortex (0.1–1 g) from male Wistar rats (150–250 g) is homogenized for 5–10 seconds in 10 mL 20 nM Hepes pH: 7.4, with an Ultra-Turrax homogenizer. The homogenizer is rinsed with 10 mL of buffer and the combined suspension centrifuged for 15 min. at 40,000×g. The pellet is washed three times with buffer. In each step the pellet is homogenized as before in 2×10 mL of buffer and centrifuged for 10 min. at 40,000×g.

The final pellet is homogenized in 20 mM Hepes pH: 7.4 (100 mL per g of original tissue) and used for binding assay.

Aliquots of 0.5 mL is added 25 μL of test solution and 25 μL of $^3$H-Oxotremorine (1.0 nM, final concentration) mixed and incubated for 30 min. at 25° C. Non-specific binding is determined in triplicate using arecoline (1 μg/mL, final concentration) as the test substance. After incubation samples are added 5 mL of ice-cold buffer and poured directly onto Whatman GF/C glass fiber filters under suction and immediately washed 2 times with 5 mL of ice-cold buffer. The amount of radioactivity on the filters are determined by conventional liquid scintillation counting. Specific binding is total binding minus non specific binding.

Test substances are dissolved in 10 mL water (if necessary heated on a steam-bath for less than 5 min.) at a concentration of 2.2 mg/mL. 25–75% inhibition of specific binding must be obtained before calculation of $IC_{50}$. The test value will be given as $IC_{50}$ (the concentration (nM) of the test substance which inhibits the specific binding of $^3$H-oxo by 50%). $IC_{50}$=(applied test substance concentration)×$(C_x/C_o-C_x)$ nM where $C_o$ is specific binding in control assays and $C_x$ is the specific binding in the test assay. (The calculations assume normal mass-action kinetics).

Furthermore the pharmacological properties of the compounds of the invention can also be illustrated by determining their capability to inhibit $^3$HPRZ (pirenzepine, [N-methyl-$^3$H]) binding to rat cerebral cortex membranes.

Pirenzepine binds selectively to subtype of muscarinic receptors. Historically the type is named the $M_1$-site, whereas pirenzepine sensitive site would be more appropriate. Although selective for $M_1$-sites pirenzepine also interact with $M_2$-sites.

All preparations are performed at 0–4° C. unless otherwise indicated. Fresh cortex (0.1–1 9) from male Wistar rats (150–200 g) is homogenized for 5–10 s in 10 mL 20 mM Hepes pH: 7.4, with an Ultra-Turrax homogenizer. The homogenizer is rinsed with 2'10 mL of buffer and the combined suspension centrifuged for 15 min. at 40,000×g. The pellet is washed three times with buffer. In each step the pellet is homogenized as before in 3×10 mL of buffer and centrifuged for 10 min. at 40,000×g.

The final pellet is homogenized in 20 mM Hepes pH: 7.4 (100 mL per g of original tissue) and used for binding assay. Aliquots of 0.5 mL is added 20 μl of test solution and 25 μL of $^3$HPRZ (1.0 nM, final conc.), mixed and incubated for 60 min. at 20° C. Non-specific binding is determined in triplicate using atropine (1 μg/mL, final conc.) as the test substance. After incubation samples are added 5 mL of ice-cold buffer and poured directly onto Whatman GF/C glass fiber filters under suction and immediately washed 2 times with 5 mL of ice-cold buffer. The amount of radioactivity on the filters are determined by conventional liquid scintillation counting. Specific binding is total binding minus non-specific binding.

Test substances are dissolved in 10 mL water, at a concentration of 0.22 mg/mL. 25–75% inhibition of specific binding must be obtained before calculation of $IC_{50}$.

The test value will be given as $IC_{50}$ (the concentration (nM) of the test substance which inhibits the specific binding of $^3$HPRZ by 50%). $IC_{50}$=(applied test substance concentration)×$(C_x/C_o-C_x)$ nM where $C_o$ is specific binding in control assays and $C_x$ is the specific binding in the test assay. (The calculations assume normal mass-action kinetics).

Additionally, the pharmacological activity and tendency to produce salivation can be determined using the following methods:

Stimulation of phosphoinositol hydrolysis in A9 L-m1 cells:

A9-L-m1 cells were cultured to confluence in 75 mL flasks containing Dubecco's modified essential media. Cells were prelabeled with 1 μCi/mL of myo[2–3H]inositol (Amersham Inc, 16.3 Ci/mmol) for 48 h prior to assay. On the day of assay, cells were detached using a 30 s exposure to 0.25% trypsin in 1 mM EDTA. The cells were collected by centrifugation (300×g for 5 min) and resuspended in oxygenated HEPES buffer containing 10 mM LiCl, 142 mM NaCl, 5.6 mM KCl, 2.2 mM $CaCl_2$, 1 mM $MgCl_2$, 3.6 mM $NaHCO_3$, 5.6 mM D-glucose, and 30 mM sodium HEPES at pH 7.4. Cells were incubated at 37 C for 45 min in the presence of varying concentrations of drug. The reaction was terminated by the addition of 3 mL of ice cold 10 mM LiCl, sonicated, and centrifugated at 20,000×g. The supernatent was decanted over a Accell QMA anion exchange SEP-PAK cartridge in the formate form (Waters Associates, Milford, Mass.). The cartridges were washed with 10 mL of $H_2O$ followed by 10 mL of 5 mM sodium borate. [3H]PI was eluted directly into scintillation vials for counting with 4 mL of 0.1 ammonium formate/0.01 mM formic acid/5 mM sodium borate. Data is expressed as the percent of total [3H]PI stimulated in the presence of 1 mM carbachol. Half-maximal values (EC50) were determined from the mean of seven point curves using a four parameter logistic model.

Salivation in mice:

Mice weighing 20 to 30 g were used for salivation testing. Mice, in groups of five, were injected i.p. with 10 mg/kg doses of compound dissolved in distilled water. After, 30 min, salivation and tremor were scored on a scale of 0, 1, or 2, where 0=no effect, 1=moderate salivation or tremor, and 2=marked salivation or tremor. Those compounds producing an average score of 1 were tested at half log lower doses until a score lower than 1 was achieved. The lowest dose of compound producing a score of 1 was expressed at the minimum effective dose (MED).

Table I illustrates several additional formula I compounds as claimed herein.

TABLE I

| R | $R^4$ | R | $R^4$ |
|---|---|---|---|
| $OR^4$ | phenyl | $SR^4$ | phenyl |
| $OR^4$ | methoxyphenyl | $SR^4$ | methoxyphenyl |
| $OR^4$ | fluorophenyl | $SR^4$ | fluorophenyl |
| $OR^4$ | chlorophenyl | $SR^4$ | chlorophenyl |
| $OR^4$ | trifluoromethylphenyl | $SR^4$ | trifluoromethylphenyl |
| $OR^4$ | N-alkylthiazolidinones | $SR^4$ | N-alkylthiazolidinones |
| $OR^4$ | N-alkyloxazolidinones | $SR^4$ | N-alkyloxazolidinones |
| $OR^4$ | S-alkylmercaptothiophenes | $SR^4$ | S-alkylmercaptothiophenes |
| $OR^4$ | benzothiophenemethyl | $SR^4$ | benzothiophenemethyl |
| $OR^4$ | 1,4-benzodioxanmethyl | $SR^4$ | 1,4-benzodioxanmethyl |
| $OR^4$ | decahydronapthyl | $SR^4$ | decahydronapthyl |
| $OR^4$ | tetrahydronapthyl | $SR^4$ | tetrahydronapthyl |
| $OR^4$ | chromanyl | $SR^4$ | chromanyl |
| $OR^4$ | allyl | $SR^4$ | allyl |
| $OR^4$ | (alkyl)allyl | $SR^4$ | (alkyl)allyl |
| $OR^4$ | cinnamyl | $SR^4$ | cinnamyl |
| $OR^4$ | phenylpropargyl | $SR^4$ | phenylpropargyl |
| $OR^4$ | methyoxyphenylpropargyl | $SR^4$ | methyoxyphenylpropargyl |
| $OR^4$ | fluorophenylpropargyl | $SR^4$ | fluorophenylpropargyl |
| $OR^4$ | chlorophenylpropargyl | $SR^4$ | chlorophenylpropargyl |
| $OR^4$ | trifluoromethyoxyphenylpropargyl | $SR^4$ | trifluoromethyoxyphenylpropargyl |
| $OR^4$ | trifluoromethylphenylpropargyl | $SR^4$ | trifluoromethylphenylpropargyl |
| $OR^4$ | indanyl | $SR^4$ | indanyl |
| $OR^4$ | methoxyindanyl | $SR^4$ | methoxyindanyl |
| $OR^4$ | fluoroindanyl | $SR^4$ | fluoroindanyl |
| $OR^4$ | chloroindanyl | $SR^4$ | chloroindanyl |
| $OR^4$ | trifluoromethoxyindanyl | $SR^4$ | trifluoromethoxyindanyl |

TABLE I-continued

| R | $R^4$ | R | $R^4$ |
|---|---|---|---|
| $OR^4$ | trifluoroindanyl | $SR^4$ | trifluoroindanyl |
| $OR^4$ | cyclopropylvinyl | $SR^4$ | cyclopropylvinyl |
| $OR^4$ | cyclobutylvinyl | $SR^4$ | cyclobutylvinyl |
| $OR^4$ | cyclopentylvinyl | $SR^4$ | cyclopentylvinyl |
| $OR^4$ | cyclohexylvinyl | $SR^4$ | cyclohexylvinyl |
| $OR^4$ | phenoxyalkyl | $SR^4$ | phenoxyalkyl |
| $OR^4$ | fluorophenoxyalkyl | $SR^4$ | fluorophenoxyalkyl |
| $OR^4$ | chlorophenoxyalkyl | $SR^4$ | chlorophenoxyalkyl |
| $OR^4$ | trifluoromethylphenoxyalkyl | $SR^4$ | trifluoromethylphenoxyalkyl |
| $OR^4$ | trifluoromethoxyphenoxyalkyl | $SR^4$ | trifluoromethoxyphenoxyalkyl |
| $OR^4$ | methoxyphenoxyalkyl | $SR^4$ | methoxyphenoxyalkyl |

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen for patients suffering from diseases in the central nervous system caused by malfunctioning of the muscarinic cholinergic system it may frequently be necessary to begin with a dosage of from about 20 to about 70 mg per day and when the condition is under control to reduce the dosage as low as from about 0.1 to about 10 mg per day. The exact dosage will depend upon the mode of administration, form in which administered, the subject to be treated and the body weight of the subject to be treated, and the preference and experience of the physician or prescribing caregiver in charge.

The route of administration may be any route, which effectively transports the active compound to the appropriate or desired site of action, such as oral or parenteral e.g. rectal, transdermal, depot, subcutaneous, intravenous, intramuscular or intranasal, the oral route being preferred.

Typical compositions include a compound of formula I or a pharmaceutically acceptable acid addition salt thereof, associated with a pharmaceutically acceptable excipient which may be a carrier, or a diluent or be diluted by a carrier, or enclosed within a carrier which can be in the form of a capsule, sachet, paper, or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents, or flavoring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 0.1 to about 100 mg in a pharmaceutically acceptable carrier per unit dosage.

The compounds of this invention may be suitable for administration to an animal. Such animals include both domestic animals, for example livestock, laboratory animals, and household pets, and non-domestic animals such as wildlife. More preferredly, the animal is a vertebrate. Most preferredly, a compound of this invention shall be administered to a mammal. It is especially preferred that the animal is a domestic mammal or a human. The most preferred mammal is a human. For such purposes, a compound of this invention may be administered as a feed additive.

In order to more fully illustrate the operation of this invention, the following formulation examples are provided. The examples are illustrative only, and are not intended to limit the scope of the invention in any way.

FORMULATION 1

A typical tablet, appropriate for use in this method, may be prepared using conventional techniques and may contain:

|  | Amount per Tablet | Concentration by Weight (%) |
|---|---|---|
| (1S,4R,6S)-(2-aza-((4-cyclo-butylethoxy-1,2,5-thiadiazol-3-yl)oxy)bicyclo[2.2.1]-heptane | 5.0 mg | 4.7 |
| Lactosum | 67.8 mg Ph. Eur. | 64.2 |
| Avicel ® | 31.4 mg | 29.8 |
| Amberlite ® | 1.0 mg | 1.0 |
| magnesium stearate | 0.25 mg | 0.3 |
|  | 105.45 mg | 100 |

FORMULATION 2

Hard gelatin capsules are prepared using the following ingredients:

|  | Amount per Tablet | Concentration by Weight (%) |
|---|---|---|
| (1S,4R,6S)-(2-aza-((4-cyclopropylmeth-oxy-1,2,5-thiadiazol-3-yl)oxy)bicyclo[2.2.1]-heptane | 0.1 mg | 0.05 |
| starch dried | 200 mg | 95.2 |
| magnesium stearate | 10 mg | 4.8 |
|  | 210.1 mg | 100 |

The above ingredients are mixed and filled into hard gelatin capsules in 210.1 mg quantities.

FORMULATION 3

Suspensions each containing 1 mg of medicament per 5 mL dose are as follows:

|  | Amount per 5 mL of suspension |
|---|---|
| (1S,4R,6S)-2-aza-((4-(3-chlorophenylmethylthio) 1,2,5-thiadiazol-3-yl)oxy) bicyclo[2.2.1]-heptane | 1 mg |
| sodium carboxymethyl cellulose | 50 mg |
| syrup | 1.25 mL |
| benzoic acid solution | 0.10 mL |
| flavor | q.v |
| color | q.v. |
| water | q.s. to 5 mL |

The medicament is passed through a No. 45 mesh U.S. sieve and mixed with the sodium carboxymethyl cellulose and syrup to form a smooth paste. The benzoic acid solution, flavor and color is diluted with some of the water and added to the paste with stirring. Sufficient water is then added to produce the required volume.

The intermediates and processes of the present invention are useful for preparing compounds having beneficial muscarinic receptor activity. The compounds of the present invention have such useful muscarinic receptor activity. Certain compounds and conditions within the scope of this invention are preferred. The following conditions, invention embodiments, and compound characteristics listed in tabular form may be independently combined to produce a variety of preferred compounds and process conditions. The following list of embodiments of this invention is not intended to limit the scope of this invention in any way.

Some prefered characteristics of compounds of formula I are:

A) R is $OR^4$;

B) R is $SR^4$;

C) $R^4$ is methyl substituted with cyclobutyl;

D) $R^4$ is $C_3$–$C_6$ alkyl;

E) $R^4$ is 5-membered heterocycle having one heterocycle selected from S and N;

F) $R^4$ is $C_3$–$C_6$ alkenyl;

G)

The invention will now be described in further detail with reference to the following examples. The examples are provided for illustrative purposes, and are not to be construed as limiting the scope of the invention in any way.

PREPARATION 1

(1S,4R,1'R)-2-(1'-Phenylethyl)-2-azabicyclo[2.2.1]hept-5-ene and (1R,4S,1'R)-2-(1'-Phenylethyl)-2-azabicyclo[2.2.1]hept-5-ene

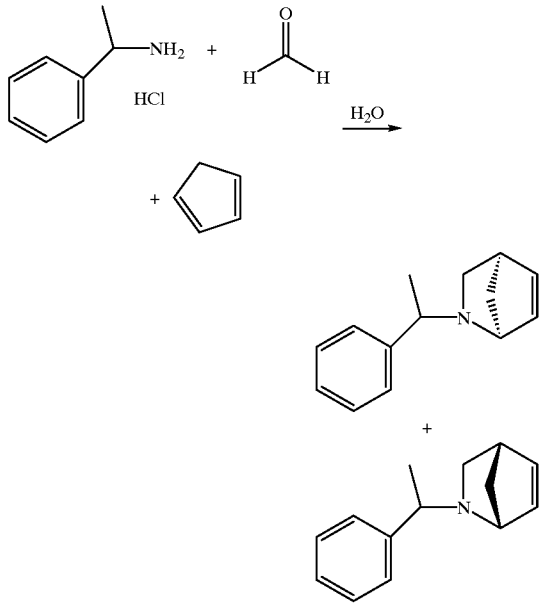

37% Aqueous formaldehyde (773.4 mmol) was added to a solution of cyclopentadiene (1.105 mol) and (R)-1-phenylethylamine hydrochloride (552.4 mmol) at $0_{13}$ C. The solution was stirred at $0_{13}$ C for 24 hours. Water (350 mL) was added to the reaction which was then washed with diethyl ether (2×250 mL). The aqueous layer was basified with solid potassium hydroxide then extracted with ethyl acetate (3×400 mL). The combined extracts were dried over magnesium sulfate, evaporated, then purified by preparative HPLC using silica gel eluting with 2 to 20% (10% triethylamine in ethanol) in ethyl acetate to yield (1S,4R,1'R)-2-(1'-phenylethyl)-2-azabicyclo[2.2.1]hept-5-ene(64.9 g/326.1 mmol) and (1R,4S,1'R)-2-(1'-phenylethyl)-2-azabicyclo[2.2.1]hept-5-ene(22 g/110.6 mmol).

PREPARATION 2

(1S,4R, 6S, 1'R)-2-(1'-Phenylethyl)-2-azabicyclo[2.2.1]heptan-6-ol and (1S,4R, 6S, 1'R)-2-(1'-Phenylethyl)-2-azabicyclo[2.2.1]heptan-5-ol

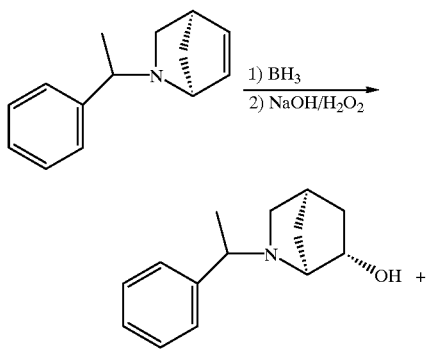

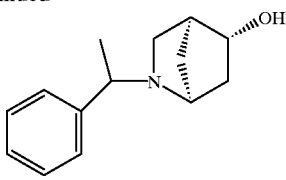

A 1.0M Borane:THF in tetrahydrofuran (628 mmol) was added to a solution of (1S,4R,1'R)-2-(1'-phenylethyl)-2-azabicyclo[2.2.1]hept-5-ene (316.6 mmol) in tetrahydrofuran (750 mL) at 0_C. Stirred at 0_C. for 2 hours whereupon water in tetrahydrofuran was added to the reaction to destroy excess borane. While keeping the reaction temperature below 10_C., 3N Aqueous sodium hydroxide (88 mL) was added to the reaction immediately followed by 30% aqueous hydrogen peroxide (147 mL). The reaction temperature was allowed to rise to 40_C. then stirred for 1.5 hours. Potassium carbonate (30 g) was added to the reaction then evaporated to remove the tetrahydrofuran. The aqueous residue was extracted with dichloromethane (3×200 mL). The organic extracts were washed with water then dried over sodium chloride/sodium sulfate then evaporated. The residue was purified by preparative HPLC using silica gel eluting with 1 to 15% (10% triethylamine in ethanol) in ethyl acetate to yield (1S,4R, 6S, 1'R)-2-(1'-phenylethyl)-2-azabicyclo[2.2.1]heptan-6-ol (32.5 g/149.8 mmol) and (1S, 4R, 6S, 1'R)-2-(1'-phenylethyl)-2-azabicyclo[2.2.1]heptan-5-ol (9.9 g/45.6 mmol).

PREPARATION 3

(1S,4R, 6S)-2-Aza-2-(t-butoxycarbonyl)-bicyclo[2.2.1]heptan-6-ol

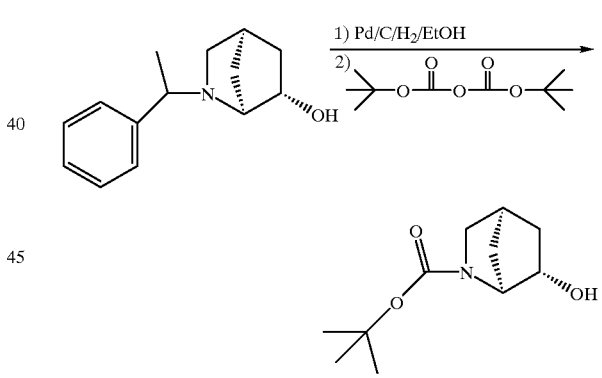

A solution of (1S,4R, 6S, 1'R)-2-(1'-phenylethyl)-2-azabicyclo[2.2.1]heptan-6-ol (30 mmol) in ethanol (150 mL) was hydrogenated with 10% Pd/C (3.3 g) at 60 PSIG of hydrogen at room temperature for 16 hours. The catalyst was filtered off and the filtrate was evaporated. A solution of the filtrate in tetrahydrofuran (100 mL) and H$_2$O (50 mL) was cooled to 0_C. The pH was adjusted to 10 with 5N aqueous sodium hydroxide. Di-t-butylcarbonate (45 mmol) was added to the reaction solution while the pH was maintained >10 with 5N aqueous sodium hydroxide. The reaction was stirred at 0_C. for four hours, poured into brine, extracted with ethyl acetate (3×150 mL), dried over sodium chloride/sodium sulfate, then evaporated. The residue was purified by preparative HPLC using silica gel eluting with 25 to 100% ethyl acetate in hexanes to yield (1S,4R, 6S)-2-Aza-2-(t-butoxycarbonyl)-bicyclo[2.2.1]heptan-6-ol (30 mmol).

EXAMPLE 1

(1S,4R, 6S)-2-Aza-2-(t-butoxycarbonyl)-6-((4-(propylthio)-1,2,5-thiadiazol-3-yl)oxy)bicyclo[2.2.1]heptane

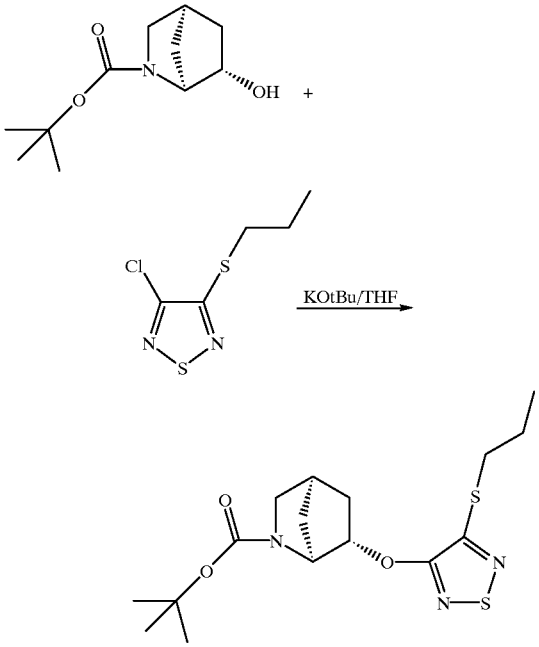

Potassium t-butoxide (39 mmol) was added to a solution of (1S,4R, 6S)-2-Aza-2-(t-butoxycarbonyl)-bicyclo[2.2.1]heptan-6-ol (30 mmol) in tetrahydrofuran (500 mL). Stirred at −5_C for 45 minutes whereupon 3-chloro-4-(propylthio)-1,2,5-thiadiazole (36 mmol) in tetrahydrofuran (100 mL) was added to the reaction. Stirred for four hours at −5_C. The reaction mixture was poured into brine and extracted with ethyl acetate (3×250 mL). The organic extracts were dried and evaporated. The residue was purified by preparative HPLC using silica gel eluting with 10 to 50% ethyl acetate in hexanes to yield (1S,4R, 6S)-2-Aza-2-(t-butoxycarbonyl)-6-((4-(propylthio)-1,2,5-thiadiazol-3-yl)oxy)bicyclo[2.2.1]heptane (4.7 g/12.7 mmol).

EXAMPLE 2

(1S,4R, 6S)-2-Aza-2-(t-butoxycarbonyl)-6-((4-propylsulfonyl-1,2,5-thiadiazol-3-yl)oxy)bicyclo[2.2.1]heptane

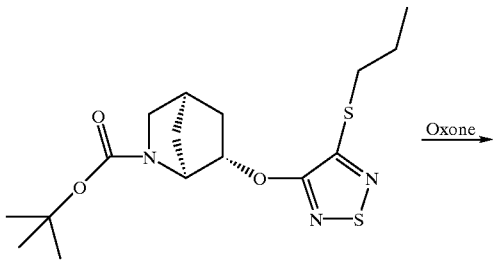

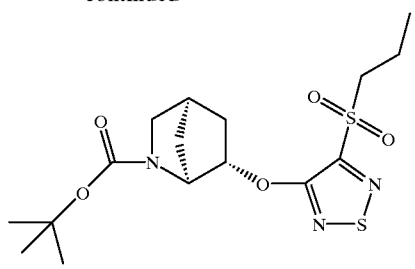

A solution of Oxone® (24.2 g/39.3 mmol) in water (75 mL) was added to a solution of (1S,4R, 6S)-2-Aza-2-(t-butoxycarbonyl)-6-((4-(propylthio)-1,2,5-thiadiazol-3-yl)oxy)bicyclo[2.2.1]heptane (4.7 g/12.7 mmol), water (25 mL), and tetrahydrofuran (75 mL). Stirred at room temperature for 16 hours. The reaction was poured into water then extracted with ethyl acetate (3×150 mL). The organic extracts were washed with a saturated sodium chloride solution and dried over sodium sulfate, then evaporated to yield LY354006, (1S,4R, 6S)-2-Aza-2-(t-butoxycarbonyl)-6-((4-propylsulfonyl-1,2,5-thiadiazol-3-yl)oxy)bicyclo[2.2.1]heptane (4.7 g/11.7 mmol).

EXAMPLE 3

(1S,4R, 6S)-2-Aza-2-(t-butoxycarbonyl)-6-((4-cyclobutylmethoxy-1,2,5-thiadiazol-3-yl)oxy)bicyclo[2.2.1]heptane

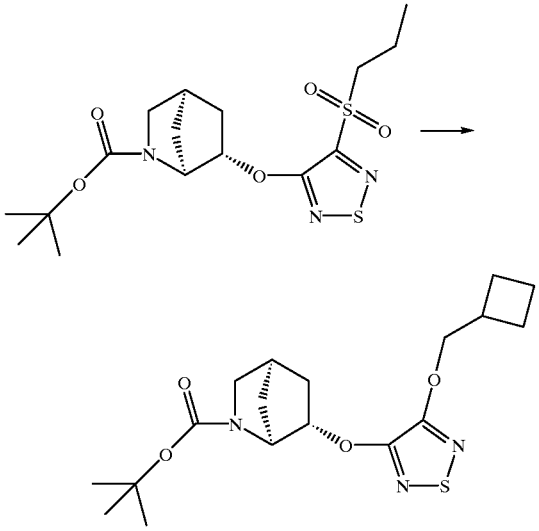

Potassium butoxide (7.8 mmol) was added to a solution of cyclobutylmethanol (10.2 mmol) and tetrahydrofuran (75 mL) was stirred for 1 hour at 0_C. The (1S,4R, 6S)-2-Aza-2-(t-butoxycarbonyl)-6-((4-propylsulfonyl-1,2,5thiadiazol-3-yl)oxy)bicyclo[2.2.1]heptane (2.5 mmol) in tetrahydrofuran (25 mL) was added to the reaction. The reaction was stirred for 2 hours at 0_C. The reaction was poured into brine then extracted with ethyl acetate (3×100 mL). The extracts were dried over magnesium sulfate then evaporated to yield (1S,4R, 6S)-2-Aza-2-(t-butoxycarbonyl)-6-((4-cyclobutylmethoxy-1,2,5-thiadiazol-3-yl)oxy)bicyclo[2.2.1]heptane (2.5 mmol).

EXAMPLE 4

(1S,4R, 6S)-2-Aza-((4-cyclobutylmethoxy-1,2,5-thiadiazol-3-yl)oxy)bicyclo[2.2.1]heptane

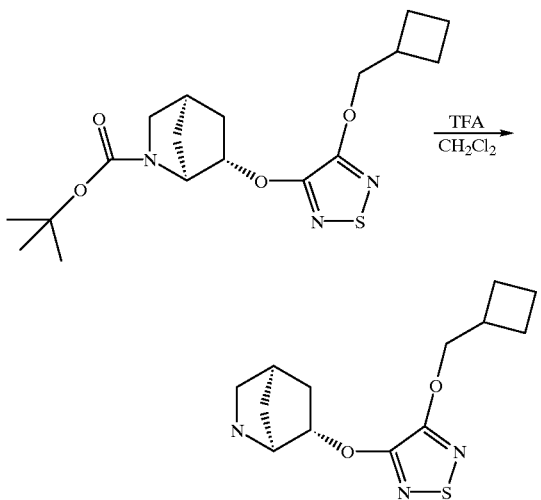

Trifluoroacetic acid (2.5 mL) was added to a solution of (1S,4R, 6S)-2-Aza-2-(t-butoxycarbonyl)-6-((4-cyclobutylmethoxy-1,2,5-thiadiazol-3-yl)oxy)bicyclo[2.2.1]heptane (2.5 mmol) in methylene chloride (40 mL) at 0_C. The reaction was stirred at 0_C. for about one hour then warmed to room temperature and stirred for sixteen hours. The reaction was concentrated on a rotary evaporator and the residue was basified with aqueous sodium bicarbonate then extracted with ethyl acetate (3×75 mL). The combined organic extracts were dried over magnesium sulfate then evaporated to yield (1S,4R, 6S)-2-Aza-((4-cyclobutylmethoxy-1,2,5-thiadiazol-3-yl)oxy)bicyclo[2.2.1]heptane which was isolated as the hydrochloride salt to yield 540 mg of the desired compound (mp=154–156_ C.).

EXAMPLE 5

The following compounds were made by following substantially the same procedure described above in Example 4, except that the corresponding starting materials were selected to provide the desired compounds.

(1S,4R, 6S)-2-Aza-((4-(2-cyclopropylethoxy)-1,2,5-thiadiazol-3-yl)oxy)bicyclo[2.2.1]heptane hydrochloride, LY354893, mp 122–123_C.

(1S,4R, 6S)-2-Aza-((4-(diphenylmethoxy)-1,2,5-thiadiazol-3-yl)oxy)bicyclo[2.2.1]heptane hydrochloride, LY368585, mp 168–171_C.

(1S,4R, 6S)-2-Aza-((4-propoxy-1,2,5-thiadiazol-3-yl)oxy)bicyclo[2.2.1]heptane hydrochloride, LY354166, mp 181–182_C.

(1S,4R, 6S)-E-2-Aza-((4-(3-phenylprop-2-eneoxy)-1,2,5-thiadiazol-3-yl)oxy)bicyclo[2.2.1]heptane hydrochloride, LY354735, mp 191–192_C.

(1S,4R, 6S)-2-Aza-((4-(3,3,3-trifluoropropoxy)-1,2,5-thiadiazol-3-yl)oxy)bicyclo[2.2.1]heptane hydrochloride, LY355169, mp 144–145_C.

(1S,4R, 6S)-2-Aza-((4-cyclopentoxy-1,2,5-thiadiazol-3-yl)oxy)bicyclo[2.2.1]heptane hydrochloride, LY357209, mp 200–202_C.

(1S,4R, 6S)-2-Aza-((4-cyclohexoxy-1,2,5-thiadiazol-3-yl)oxy)bicyclo[2.2.1]heptane hydrochloride, LY357633, mp 193–195_C.

(1S,4R, 6S)-2-Aza-((4-(1-methylethoxy)-1,2,5-thiadiazol-3-yl)oxy)bicyclo[2.2.1]heptane hydrochloride, LY357817, mp 179–180_C.

(1S,4R, 6S)-2-Aza-((4-(2-cyclopropylethoxy)-1,2,5-thiadiazol-3-yl)oxy)bicyclo[2.2.1]heptane hydrochloride, LY357834, mp 171–173_C.

(1S,4R, 6S)-2-Aza-((4-(2-methylpropoxy)-1,2,5-thiadiazol-3-yl)oxy)bicyclo[2.2.1]heptane hydrochloride, LY357878, mp 146–148_C.

(1S,4R, 6S)-2-Aza-((4-cyclobutoxy-1,2,5-thiadiazol-3-yl)oxy)bicyclo[2.2.1]heptane hydrochloride, LY357879, mp 204–206_C.

(1S,4R, 6S)-2-Aza-((4-heptoxy-1,2,5-thiadiazol-3-yl)oxy)bicyclo[2.2.1]heptane hydrochloride, LY357880, mp 186–187_C.

(1S,4R, 6S)-2-Aza-((4-(3-methylbutoxy)-1,2,5-thiadiazol-3-yl)oxy)bicyclo[2.2.1]heptane hydrochloride, LY359056, mp 167–168_C.

(1S,4R, 6S)-2-Aza-((4-cyclohexylmethoxy-1,2,5-thiadiazol-3-yl)oxy)bicyclo[2.2.1]heptane hydrochloride, LY359166, mp 168–169_C.

(1S,4R, 6S)-2-Aza-((4-cyclopentylmethoxy-1,2,5-thiadiazol-3-yl)oxy)bicyclo[2.2.1]heptane hydrochloride, LY359167, mp 169–170_C.

(1S,4R, 6S)-2-Aza-((4-(2-cyclohexylethoxy)-1,2,5-thiadiazol-3-yl)oxy)bicyclo[2.2.1]heptane hydrochloride, LY359491, mp 169–171_C.

(1S,4R, 6S)-2-Aza-((4-(2-oxetane-2-methylethoxy)-1,2,5-thiadiazol-3-yl)oxy)bicyclo[2.2.1]heptane hydrochloride, LY359684, mp 115–118_C.

(1S,4R, 6S)-2-Aza-((4-cycloheptylmethoxy-1,2,5-thiadiazol-3-yl)oxy)bicyclo[2.2.1]heptane hydrochloride, LY359686, mp 183–185_C.

EXAMPLE 6

Substantially the same procedure described above in Example 4 was used to make the following compounds, except (S)-1-phenylethylamine hydrochloride was used as the starting material.

(1R,4S,6R)-2-Aza-((4-cyclobutylmethoxy-1,2,5-thiadiazol-3-yl)oxy)bicyclo[2.2.1]heptane hydrochloride, LY353547, mp 142–44_C.

(1R,4S,6R)-2-Aza-((4-(2-cyclopropylethoxy)-1,2,5-thiadiazol-3-yl)oxy)bicyclo[2.2.1]heptane hydrochloride, LY353548, mp 112–115_C.

(1R,4S,6R)-2-Aza-((4-propoxy-1,2,5-thiadiazol-3-yl)oxy)bicyclo[2.2.1]heptane hydrochloride, LY354398, mp 177–179_C.

(1R,4S,6R,1'R,4'S,6'R)-3,4-Di-((2-azabicyclo[2.2.1]heptan-6-yl)oxy)-1,2,5-thiadiazole, LY359681, mp 186_C.

EXAMPLE 7

(1S,4R, 6S)-2-Aza-2-(t-butoxycarbonyl)-6-((4-(4-chlorophenylmethylthio)-1,2,5-thiadiazol-3-yl)oxy)bicyclo[2.2.1]heptane

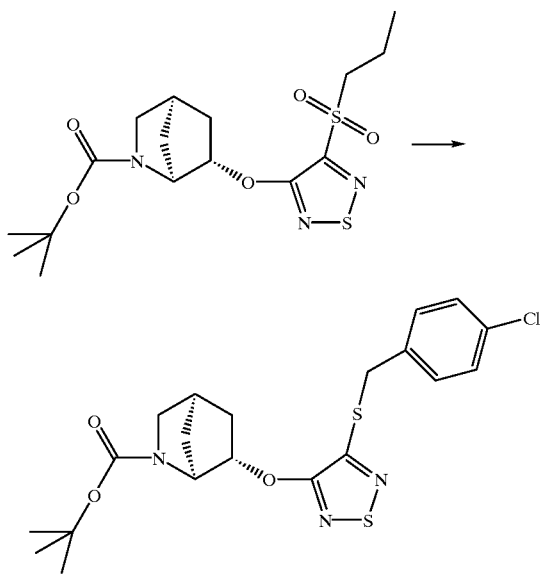

Sodium sulfide nonahydrate (3.9 mmol) was added to a solution of (1S,4R, 6S)-2-aza-2-(t-butoxycarbonyl)-6-((4-propylsulfonyl-1,2,5-thiadiazol-3-yl)oxy)bicyclo[2.2.1]heptane (2.5 mmol) in dimethylformamide (20 mL). The reaction was heated at 100_C. for one hour whereupon 4-chlorobenzyl chloride (3.9 mmol) in dimethylformamide (5 mL) was added to the reaction then heated at 100_C. for an additional three hours. The reaction was poured into brine then extracted with ethyl acetate (3×75 mL). The organic extracts were dried over magnesium sulfate then evaporated. The residue was purified by radial chromatography using silica gel eluting with 20% ethyl acetate in hexanes to yield (1S,4R, 6S)-2-Aza-2-(t-butoxycarbonyl)-6-((4-(4-chlorophenylmethylthio)-1,2,5-thiadiazol-3-yl)oxy)bicyclo[2.2.1]heptane (0.9 g/2.0 mmol).

EXAMPLE 8

(1S,4R, 6S)-2-Aza-((4-(4-chlorophenylmethylthio)-1,2,5-thiadiazol-3-yl)oxy)bicyclo[2.2.1]heptane

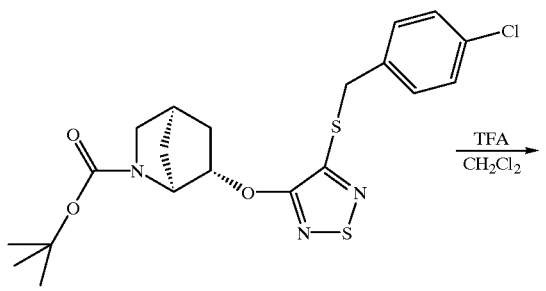

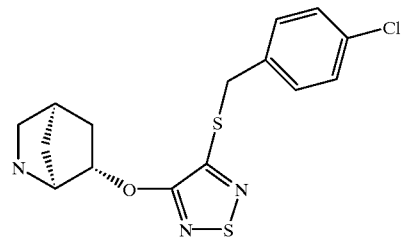

Trifluoroacetic acid (2.0 mL) was added to a solution of (1S,4R, 6S)-2-Aza-((4-(4-chlorophenylmethylthio)-1,2,5-thiadiazol-3-yl)oxy)bicyclo[2.2.1]heptane (2.0 mmol) in methylene chloride (40 mL) at 0_C. The reaction was stirred at 0_C. for one hour then warmed to room temperature and stirred for sixteen hours. The reaction was concentrated on a rotary evaporator and the residue was basified with aqueous sodium bicarbonate then extracted with ethyl acetate (3×75 mL). The combined organic extracts were dried over magnesium sulfate then evaporated to yield (1S,4R, 6S)-2-aza-((4-(4-chlorophenylmethylthio)-1,2,5-thiadiazol-3-yl)oxy)bicyclo[2.2.1]heptane which was isolated as the hydrochloride salt to yield 620 mg of LY359057 (mp=211–212_C).

EXAMPLE 9

The following compounds were prepared using substantially the same procedure as described above in Example 8.

(1S,4R, 6S)-2-Aza-((4-cyclobutylmethylthio-1,2,5-thiadiazol-3-yl)oxy)bicyclo[2.2.1]heptane hydrochloride, LY359058, mp 144–146_C.

(1S,4R, 6S)-2-Aza-((4-(4-fluorophenylmethylthio)-1,2,5-thiadiazol-3-yl)oxy)bicyclo[2.2.1]heptane hydrochloride, LY359683, mp 165–169_C.

(1S,4R, 6S)-2-Aza-((4-(2-cyclopropylethylthio)-1,2,5-thiadiazol-3-yl)oxy)bicyclo[2.2.1]heptane hydrochloride, LY359685, mp 121–123_C.

(1S,4R, 6S)-2-Aza-2-(t-butoxycarbonyl)-((4-(2-thienylthio)-1,2,5-thiadiazol-3-yl)oxy)bicyclo[2.2.1]heptane

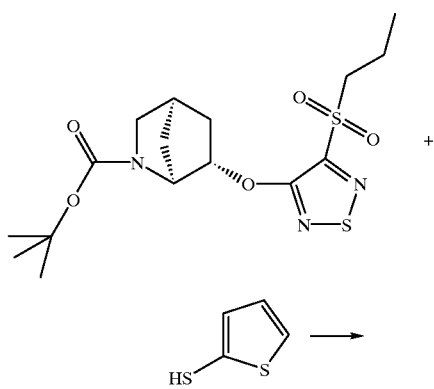

25
-continued

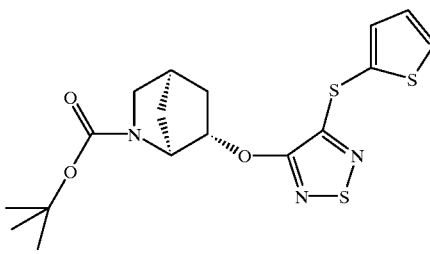

Potassium carbonate (2.1 mmol) was added to a solution 2-mercaptothiophene (4.0 mmol) in dimethylformamide (25 mL) heated at 75_C. Stirred for one hour whereupon (1S,4R, 6S)-2-Aza-2-(t-butoxycarbonyl)-6-((4-propylsulfonyl-1,2,5-thiadiazol-3-yl)oxy)bicyclo[2.2.1] heptane (2.0 mmol) in dimethylformamide (5 mL) was added to the reaction and stirred for sixteen hours at 75_C. The reaction was poured into brine then extracted with ethyl acetate (3×75 mL). The organic extracts were dried over magnesium sulfate then evaporated. The residue was purified by radial chromatography using silica gel eluting with 25% ethyl acetate in hexanes to yield (1S,4R, 6S)-2-Aza-2-(t-butoxycarbonyl)-((4-(2-thienylthio)-1,2,5-thiadiazol-3-yl)oxy)bicyclo[2.2.1]heptane (0.26 g/0.6 mmol).

EXAMPLE 11

(1S,4R, 6S)-2-Aza-((4-(2-thienylthio)-1,2,5-thiadiazol-3-yl)oxy)bicyclo[2.2.1]heptane

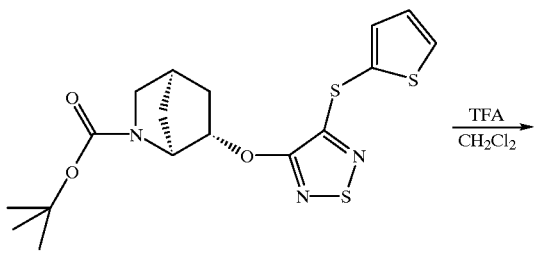

Trifluoroacetic acid (0.6 mL) was added to a solution of (1S,4R, 6S)-2-Aza-2-(t-butoxycarbonyl)-((4-(2-thienylthio)-1,2,5-thiadiazol-3-yl)oxy)bicyclo[2.2.1]heptane (0.6 mmol) in methylene chloride (50 mL) The reaction was stirred at room temperature for sixteen hours. The reaction was concentrated on a rotary evaporator and the residue was basified with aqueous sodium bicarbonate then extracted with ethyl acetate (3×75 mL). The combined organic extracts were dried over magnesium sulfate then evaporated to yield (1S,4R, 6S)-2-Aza-((4-(2-thienylthio)-1,2,5-thiadiazol-3-yl)oxy)bicyclo[2.2.1]heptane which was isolated as the hydrochloride salt to yield 140 mg of LY359682 (mp=174–180_C.)

[exo] 2-Aza-2-(t-butoxycarbonyl)-5-((4-propylthio-1,2,5-thiadiazol-3-yl)oxy)bicyclo[2.2.1]heptane Preparation of:

26
2-Aza-2-(t-butoxycarbonyl)-bicyclo[2.2.1]hept-5-ene

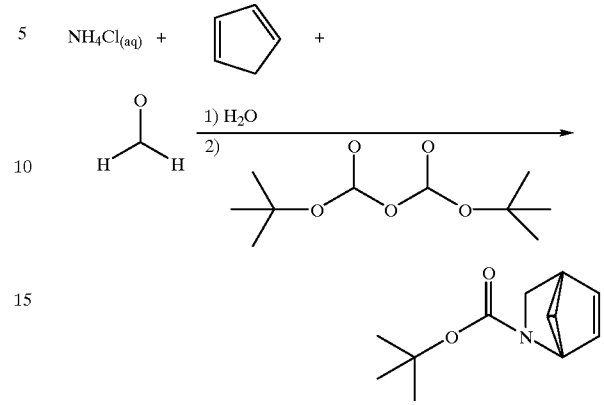

Cyclopentadiene (1.20 mol) was added to a solution of saturated aqueous ammonium chloride (257 mL) and 37% aqueous formaldehyde (0.84 mol). The solution was stirred at room temperature for 16 hours. Water (130 mL) was added to the reaction then washed with diethyl ether (2×150 mL). The aqueous layer was basified with solid potassium hydroxide. Di-t-butyldicarbonate (1.00 mol) was added to the aqueous layer while maintaining the pH between 9.5 and 10. Stirred overnight at room temperature. The reaction was extracted with ethyl acetate (3×500 mL). The combined extracts were washed with a saturated sodium chloride solution and dried over sodium sulfate then evaporated. The residue was purified by preparative HPLC over silica gel eluting with 25 to 75% ethyl acetate in hexanes to yield 2-aza-2-(t-butoxycarbonyl)-bicyclo[2.2.1]hept-5-ene (62 g/318 mmol).

[exo] 2-Aza-2-(t-butoxycarbonyl)-bicyclo[2.2.1] heptan-5-ol and [exo] 2-Aza-2-(t-butoxycarbonyl)-bicyclo[2.2.1]heptan-6-ol

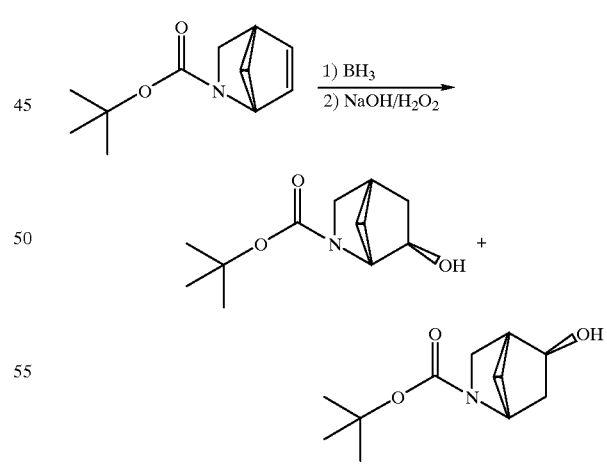

1.0M Borane:THF in tetrahydrofuran (626 mmol) was added to a solution of 2-aza-2-(t-butoxycarbonyl)-bicyclo [2.2.1]hept-5-ene (315 mmol) in tetrahydrofuran (700 mL) at 0_C. Stirred at 0_C. for 2 hours whereupon water in tetrahydrofuran was added to the reaction to destroy excess borane. While keeping the reaction temperature below 10_C., 3N Aqueous sodium hydroxide (88 mL) was added to the reaction immediately followed by 30% aqueous hydrogen peroxide (148 mL). The reaction temperature was allowed to rise to 40_C. then stirred for 1.5 hours. Potassium carbonate (30 g) was added to the reaction then evaporated to remove the tetrahydrofuran. The aqueous residue was extracted with dichloromethane. The organic extracts were washed with a saturated sodium chloride solution then dried over sodium sulfate then evaporated. The residue was purified by preparative HPLC using silica gel eluting with 10 to 75% ethyl acetate in hexanes to yield [exo] 2-aza-2-(t-butoxycarbonyl)-bicyclo[2.2.1]heptan-5-ol (14.0 g/65.7 mmol) and [exo] 2-aza-2-(t-butoxycarbonyl)-bicyclo[2.2.1]heptan-6-ol (14.5 g/68.1 mmol).

[exo] 2-Aza-2-(t-butoxycarbonyl)-5-((4-propylthio-1,2,5-thiadiazol-3-yl)oxy)bicyclo[2.2.1]heptane

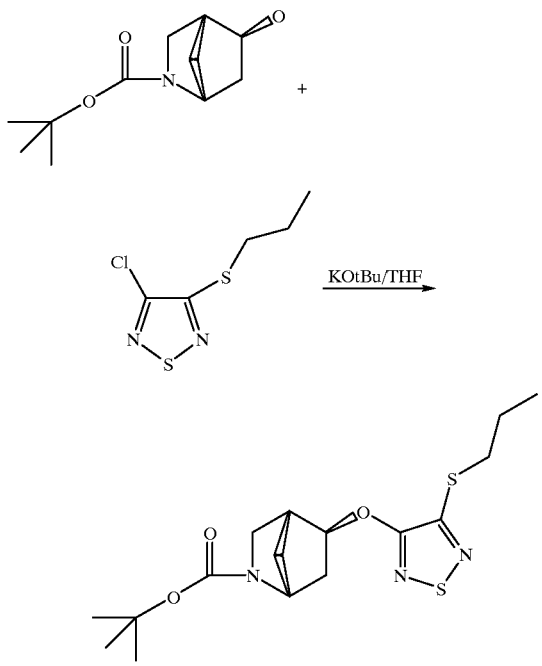

Potassium t-butoxide (56.3 mmol) was added to a solution of [exo] 2-aza-2-(t-butoxycarbonyl)-bicyclo[2.2.1]heptan-5-ol (56.3 mmol) in tetrahydrofuran (550 mL) at room temperature. Stirred for one hour whereupon the reaction was cooled to −10_C. and 3-chloro-4-propylthio-1,2,5-thiadiazole (13.1/67.6 mmol) in tetrahydrofuran (50 mL). The reaction was stirred at −10_C. for four hours then the reaction was poured into brine then extracted with ethyl acetate (3×500 mL). The combined organic extracts were washed woth a sautrated sodium chloride solution and dried over sodium sulfate, then evaporated. The residue was purified by preparative HPLC using silica gel eluting with 15 to 60% ethyl acetate in hexanes to yield [exo] 2-aza-2-(t-butylcarbonyl)-5-((4-propylthio-1,2,5-thiadiazol-3-yl)oxy)bicyclo[2.2.1]heptane (5.3 g/14.3 mmol)

EXAMPLE 13

[exo] 2-Aza-2-(t-butoxycarbonyl)-5-((4-propylsulfonyl-1,2,5-thiadiazol-3-yl)oxy)bicyclo[2.2.1]heptane

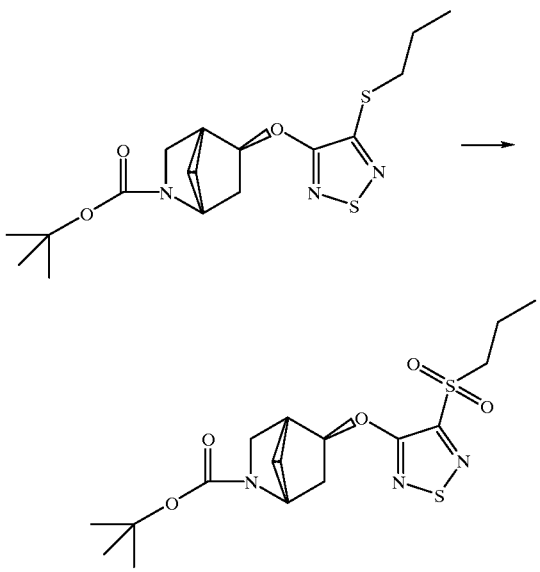

A solution of Oxone® (26.4 g/14.3 mmol) in water (120 mL) was added to a solution of [exo] 2-aza-2-(t-butylcarbonyl)-5-((4-propylthio-1,2,5-thiadiazol-3-yl)oxy)bicyclo[2.2.1]heptane (4.7 g/12.7 mmol) and tetrahydrofuran (80 mL). Stirred at room temperature for 16 hours. The reaction was poured into water then extracted with ethyl acetate (3×150 mL). The organic extracts were washed with a saturated sodium chloride solution and dried over sodium sulfate, then evaporated to yield [exo] 2-aza-2-(t-butoxycarbonyl)-5-((4-propylsulfonyl-1,2,5-thiadiazol-3-yl)oxy)bicyclo[2.2.1]heptane (5.5 g/14.3 mmol).

EXAMPLE 14

[exo]2-Aza-2-(t-butoxycarbonyl)-5-((4-cyclobutylmethylthio-1,2,5-thiadiazol-3-yl)oxy)bicyclo[2.2.1]heptane

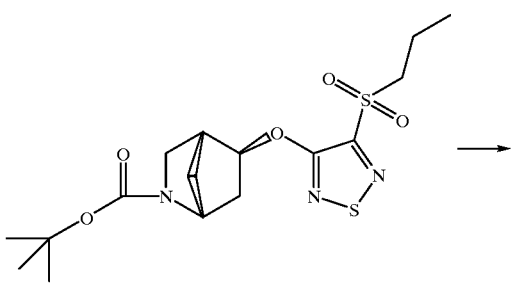

-continued

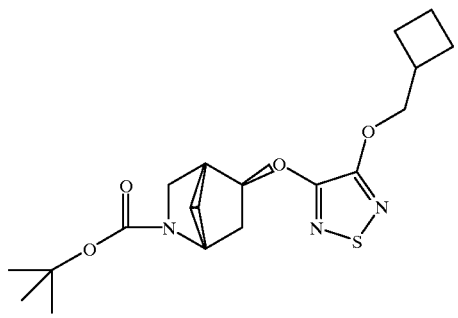

Potassium butoxide (6.0 mmol) was added to a solution of cyclobutylmethanol (7.0 mmol) and tetrahydrofuran (75 mL) at 0_C. The reaction was stirred for 1 hour at 0_C. [exo] 2-Aza-2-(t-butoxycarbonyl)-5-((4-propylsulfonyl-1,2,5-thiadiazol-3-yl)oxy)bicyclo[2.2.1]heptane (2.0 mmol) in tetrahydrofuran (25 mL) was added to the reaction. The reaction was stirred for 2 hours at 0_C. The reaction was poured into brine then extracted with ethyl acetate (3×100 mL). The extracts were dried over magnesium sulfate then evaporated to yield [exo] 2-aza-2-(t-butoxycarbonyl)-5-((4-cyclobutylmethoxy-1,2,5-thiadiazol-3-yl)oxy)bicyclo [2.2.1]heptane (2.5 mmol).

EXAMPLE 15

[exo]2-Aza-5-((4-propylthio-1,2,5-thiadiazol-3-yl)oxy)bicyclo[2.2.1]heptane

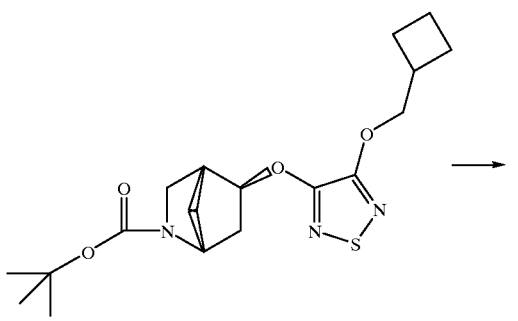

Trifluoroacetic acid (2.0 mL) was added to a solution of [exo]-2-aza-2-(t-butoxycarbonyl)-5-((4-cyclobutylmethoxy-1,2,5-thiadiazol-3-yl)oxy)bicyclo [2.2.1]heptane (2.0 mmol) in methylene chloride (50 mL) at 0_C. The reaction was stirred at 0_C. for one hour then warmed to room temperature and stirred for sixteen hours. The reaction was concentrated on a rotary evaporator and the residue was basified with aqueous sodium bicarbonate then extracted with ethyl acetate (3×75 mL). The combined organic extracts were dried over magnesium sulfate then evaporated to yield [exo]-2-aza-5-((4-cyclobutylmethoxy-1,2,5-thiadiazol-3-yl)oxy)bicyclo[2.2.1]heptane which was isolated as the hydrochloride salt to yield 540 mg of LY354889 (mp=146–149_C.).

EXAMPLE 16

The following compounds were prepared using substantially the same procedure as described above in Example 15.

[exo]-2-aza-5-((4-hexoxy-1,2,5-thiadiazol-3-yl)oxy) bicyclo[2.2.1]heptane hydrochloride, LY355776, mp 130–135_C.

[exo]-2-aza-5-((4-(2-methylpropoxy)-1,2,5-thiadiazol-3-yl)oxy)bicyclo[2.2.1]heptane hydrochloride, LY359977, mp 142–144_C.

[exo]-2-aza-5-((4-(4-fluorophenylmethoxy)-1,2,5-thiadiazol-3-yl)oxy)bicyclo[2.2.1]heptane hydrochloride, LY362269, mp 165–167_C.

ENDO-2-Aza-2-(t-butoxycarbonyl)-6-((4-(propylthio)-1,2,5-thiadiazol-3-yl)oxy)bicyclo[2.2.1] heptane Preparation of 2-Aza-2-(t-butoxycarbonyl)bicyclo [2.2.1]heptan-6-one

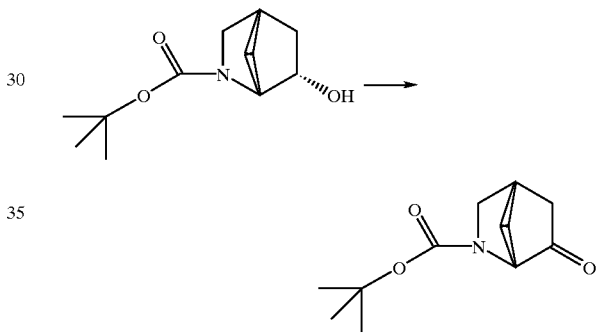

Dimethylsulfoxide (169.3 mmol) was added to a solution of oxalyl chloride (77.9 mmol) in dichloromethane (275 mL) at −78_C. Stirred for 20 minutes whereupon [endo]2-aza-2-(t-butoxycarbonyl)-bicyclo[2.2.1]heptan-6-ol (15.0 g/70.4 mmol) in dichloromethane (25 mL). Stirred at −78_ C. for 3 hours then triethylamine (352 mmol) was added to the reaction then warmed to room temperature for one hour. Brine (150 mL) was added then the reaction was extracted with dichloromethane (3×200 mL). The organic extracts were dried over magnesium sulfate then evaporated. The residue was purified by flash chromatagraphy over silica gel eluting with 25% ethyl acetate in hexanes to yield 2-aza-2-(t-butoxycarbonyl)-bicyclo[2.2.1]heptan-6-one (12.6 g/59.7 mmol).

[endo]-2-Aza-2-(t-butoxycarbonyl)bicyclo[2.2.1] heptan-6-ol

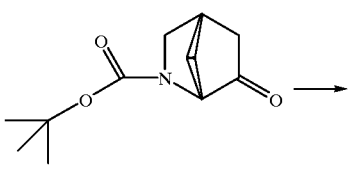

-continued

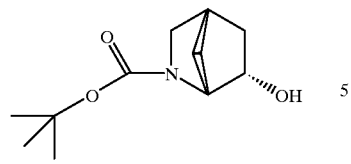

L-Selectride (151 mmol) was added to a solution of 2-aza-2-(t-butoxycarbonyl)-bicyclo[2.2.1]heptan-6-one (59.7 mmol) in tetrahydrofuran (300 mL) at −78__C. Stirred for three hours at −78__C. then warmed to 0__C. whereupon 3N aqueous sodium hydroxide (67 mL) followed by 30% aqueous hydrogen peroxide (33 mL). Stirred at room temperature for two hours then evaporated the tetrahydrofuran. The residue was extracted with dichloromethane (3×150 mL). Dried the organic extracts over magnesium sulfate then evaporated. The residue was purified by preprative HPLC using silica gel eluting with 10% to 50% ethyl acetate in hexanes to yield [endo] 2-aza-2-benzylbicyclo[2.2.1] heptan-6-ol (12 g/56.3 mmol).

ENDO-2-Aza-2-(t-butoxycarbonyl)-6-((4-(propylthio)-1,2,5-thiadiazol-3-yl)oxy)bicyclo[2.2.1]heptane

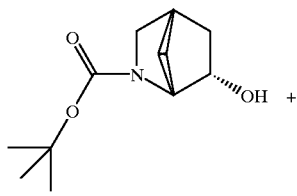

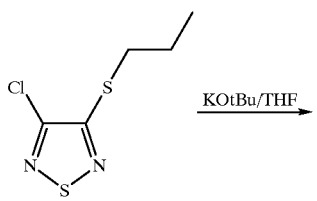

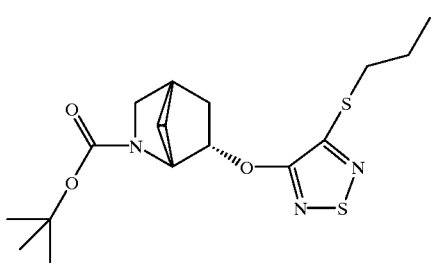

Postassium t-butoxide (56.3 mmol) was added to a solution of [endo]-2-aza-2-(t-butoxycarbonyl)-bicyclo[2.2.1] heptan-6-ol (56.3 mmol) in tetrahydrofuran (500 mL). Stirred at −5__C for 45 minutes whereupon 3-chloro-4-(propylthio)-1,2,5-thiadiazole (67.6 mmol) in tetrahydrofuran (100 mL) was added to the reaction. Stirred for four hours at −5__C. Poured the reaction into brine and extracted with ethyl acetate (3×250 mL). The organic extracts were washed with a saturated sodium chloride solution and dried over sodium sulfate then evaporated. The residue was purified by preprative HPLC using silica gel eluting with 10 to 75% ethyl acetate in hexanes to yield [endo]-2-aza-2-(t-butoxycarbonyl)-6-((4-(propylthio)-1,2,5-thiadiazol-3-yl)oxy)bicyclo[2.2.1]heptane (2.6 g/7.0 mmol).

EXAMPLE 18

[endo]-2-Aza-2-(t-butoxycarbonyl)-6-((4-propylsulfonyl-1,2,5-thiadiazol-3-yl)oxy)bicyclo[2.2.1]heptane

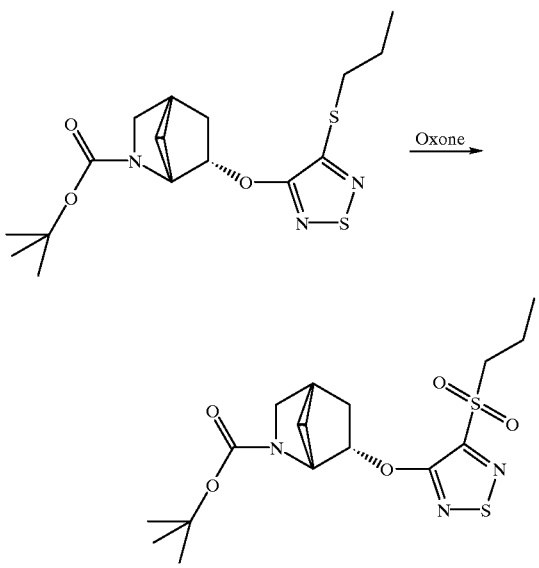

A solution of Oxone® (12.9 g/21.0 mmol) in water (40 mL) was added to a solution of [endo]-2-aza-2-(t-butoxycarbonyl)-6-((4-(propylthio)-1,2,5-thiadiazol-3-yl) oxy)bicyclo[2.2.1]heptane (7.0 mmol), water (20 mL), and tetrahydrofuran (40 mL). Stirred at room temperature for 16 hours. The reaction was poured into water then extracted with ethyl acetate (3×150 mL). The organic extracts were washed with a saturated sodium chloride solution and dried over sodium sulfate, then evaporated to yield [endo]-2-aza-2-(t-butoxycarbonyl)-6-((4-propylsulfonyl-1,2,5-thiadiazol-3-yl)oxy)bicyclo[2.2.1]heptane (2.5 g/6.2 mmol).

EXAMPLE 19

[endo]-2-Aza-2-(t-butoxycarbonyl)-6-((4-cyclobutylmethoxy-1,2,5-thiadiazol-3-yl)oxy) bicyclo[2.2.1]heptane

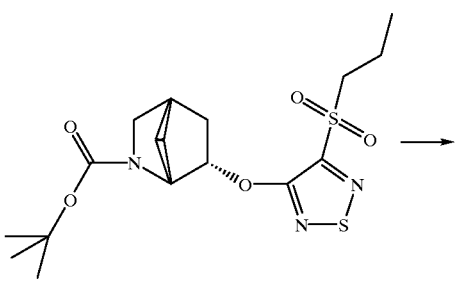

-continued

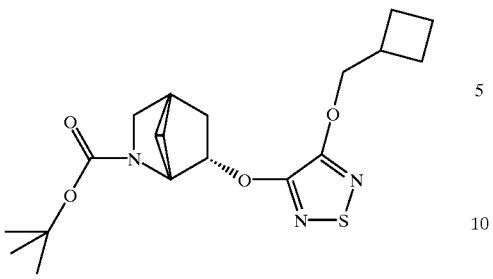

Potassium butoxide (3.1 mmol) was added to a solution of cyclobutylmethanol (4.8 mmol) and tetrahydrofuran (75 mL) at 0_C. The reaction was stirred for 1 hour at 0_C. [endo]-2-aza-2-(t-butoxycarbonyl)-6-((4-propylsulfonyl-1,2,5-thiadiazol-3-yl)oxy)bicyclo[2.2.1]heptane (1.2 mmol) in tetrahydrofuran (25 mL) was added to the reaction. The reaction was stirred for 2 hours at 0_C. The reaction was poured into brine then extracted with ethyl acetate (3×100 mL). The extracts were dried over magnesium sulfate then evaporated to yield [endo]-2-aza-2-(t-butoxycarbonyl)-6-((4-cyclobutylmethoxy-1,2,5-thiadiazol-3-yl)oxy)bicyclo[2.2.1]heptane (0.45 g/1.2 mmol).

EXAMPLE 20

[endo]-2-Aza-((4-cyclobutylmethoxy-1,2,5-thiadiazol-3-yl)oxy)bicyclo[2.2.1]heptane

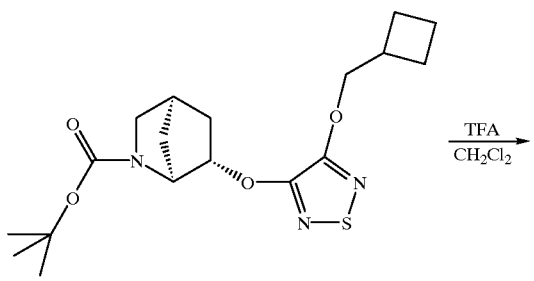

Trifluoroacetic acid (1.2 mL) was added to a solution of [endo]-2-aza-2-(t-butoxycarbonyl)-6-((4-cyclobutylmethoxy-1,2,5-thiadiazol-3-yl)oxy)bicyclo[2.2.1]heptane (1.2 mmol) in methylene chloride (35 mL) and stirred at room temperature for sixteen hours. The reaction was concentrated on a rotary evaporator and the residue was basified with aqueous sodium bicarbonate then extracted with ethyl acetate (3×75 mL). The combined organic extracts were dried over magnesium sulfate then evaporated to yield [endo]-2-aza-6-((4-cyclobutylmethoxy-1,2,5-thiadiazol-3-yl)oxy)bicyclo[2.2.1]heptane which was isolated as the hydrochloride salt to yield 200 mg of LY362567 (mp=158–160_C.).

EXAMPLE 21

The following compounds were prepared using substantially the same procedure as described above in Example 20.

[endo]-2-aza-6-((4-(4-fluorophenylmethoxy)-1,2,5-thiadiazol-3-yl)oxy)bicyclo[2.2.1]heptane hydrochloride, LY362519, mp 176–178_C.

EXAMPLE 22

[exo]2-Aza-5-((4-propylsulfonyl-1,2,5-thiadiazol-3-yl)oxy)bicyclo[2.2.1]heptane

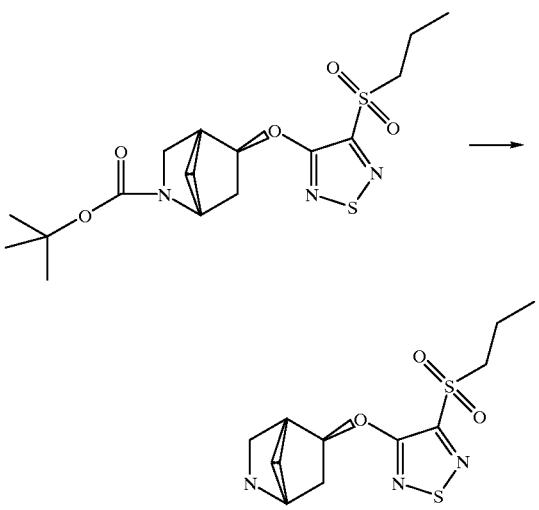

Trifluoroacetic acid (3.0 mL) was added to a solution of [exo]-2-aza-2-(t-butoxycarbonyl)-5-((4-propylsulfonyl-1,2,5-thiadiazol-3-yl)oxy)bicyclo[2.2.1]heptane (3.0 mmol) in methylene chloride (10 mL) at 0_C. The reaction was stirred at 0_C. for four hours then warmed to room temperature and stirred for sixteen hours. The reaction was concentrated on a rotary evaporator and the residue was taken up in 1N HCl(aq), washed with diethyl ether, basified with aqueous potassium carbonate then extracted with ethyl acetate (3×100 mL). The combined organic extracts were dried over magnesium sulfate then evaporated to yield [exo]-2-aza-5-((4-propylsulfonyl-1,2,5-thiadiazol-3-yl)oxy)bicyclo[2.2.1]heptane (2.3 mmol).

EXAMPLE 23

[exo]2-Aza-5-((4-(2-cyclopropylethoxy)-1,2,5-thiadiazol-3-yl)oxy)bicyclo[2.2.1]heptane

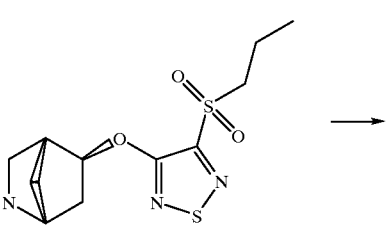

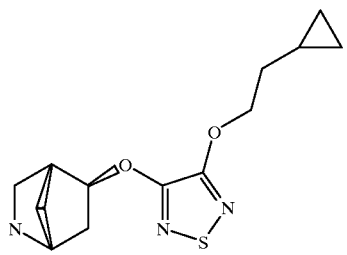

Potassium butoxide (6.9 mmol) was added to a solution of 2-cyclopropylethanol (6.9 mmol) and tetrahydrofuran (30 mL) room temperature. The reaction was stirred for one hour then [exo] 2-aza-5-((4-propylsulfonyl-1,2,5-thiadiazol-3-yl)oxy)bicyclo[2.2.1]heptane (2.3 mmol) in tetrahydrofuran (5 mL) was added to the reaction. The reaction was stirred for sixteen hours at room temperature. The reaction was concentrated on a rotary evaporator and the residue was taken up in 1N HCl(aq), washed with diethyl ether, basified with aqueous potassium carbonate then extracted with ethyl acetate (3×75 mL). The extracts were dried over magnesium sulfate then evaporated and the residue was purified by radial chromatography eluting with 1% aqueous ammonium hydroxide/10% ethanol in chloroform to yield [exo] 2-aza-5-((4-(2-cyclopropylethoxy)-1,2,5-thiadiazol-3-yl)oxy)bicyclo[2.2.1]heptane which was isolated as the hydrochloride salt to yield 450 mg of LY349456 (mp=143–144__C.).

EXAMPLE 24

(1S,4R, 6S)-2-Aza-((4-(2-thienylthio)-1,2,5-thiadiazol-3-yl)oxy)bicyclo[2.2.1]heptane

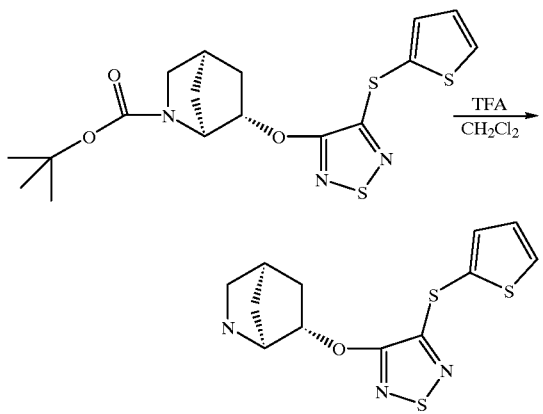

Trifluoroacetic acid (0.6 mL) was added to a solution of (1S,4R, 6S)-2-Aza-2-(t-butoxycarbonyl)-((4-(2-thienylthio)-1,2,5-thiadiazol-3-yl)oxy)bicyclo[2.2.1]heptane (0.6 mmol) in methylene chloride (50 mL) The reaction was stirred at room temperature for sixteen hours. The reaction was concentrated on a rotary evaporator and the residue was basified with aqueous sodium bicarbonate then extracted with ethyl acetate (3–75 mL). The combined organic extracts were dried over magnesium sulfate then evaporated to yield (1S,4R, 6S)-2-Aza-((4-(2-thienylthio)-1,2,5-thiadiazol-3-yl)oxy)bicyclo[2.2.1]heptane which was isolated as the hydrochloride salt to yield 140 mg of LY359682 (mp=174–180__C.).

EXAMPLE 25

Substantially the same procedure described above in Example 24 was used to make the following compounds, except (S)-1-phenylethylamine hydrochloride was used as the starting material.

(1R,4S,6R)-2-Aza-((4-(4-fluorophenylthio)-1,2,5-thiadiazol-3-yl)oxy)bicyclo[2.2.1]heptane hydrochloride, LY366961, mp 149–151__C.

EXAMPLE 26

ENDO-2-Aza-2-(t-butoxycarbonyl)-5-((4-(propylthio)-1,2,5-thiadiazol-3-yl)oxy)bicyclo[2.2.1]heptane Preparation of 2-Aza-2-(t-butoxycarbonyl)bicyclo[2.2.1]heptan-5-one

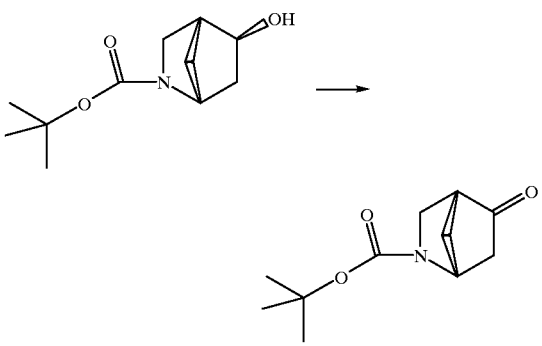

Dimethylsulfoxide (85.9 mmol) was added to a solution of oxalyl chloride (39.5 mmol) in dichloromethane (100 mL) at −78__C. Stirred for 20 minutes whereupon [exo]2-aza-2-(t-butoxycarbonyl)-bicyclo[2.2.1]heptan-5-ol (35.7 mmol) in dichloromethane (50 mL). Stirred at −78__C. for 3 hours then triethylamine (179 mmol) was added to the reaction then warmed to room temperature for one hour. Brine was added then the reaction was extracted with dichloromethane (3×200 mL). The organic extracts were dried over magnesium sulfate then evaporated. The residue was purified by preparative HPLC over silica gel eluting with 10% to 75% ethyl acetate in hexanes to yield 2-aza-2-(t-butoxycarbonyl)-bicyclo[2.2.1]heptan-5-one (31.3 mmol).

[endo]-2-Aza-2-(t-butoxycarbonyl)bicyclo[2.2.1]heptan-5-ol

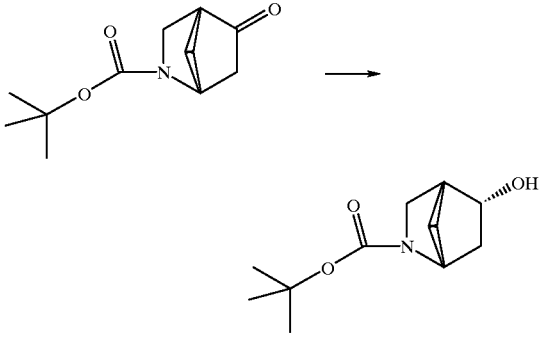

L-Selectride (79 mmol) was added to a solution of 2-aza-2-(t-butoxycarbonyl)-bicyclo[2.2.1]heptan-5-one (31.3 mmol) in tetrahydrofuran (160 mL) at −78__C. Stirred for three hours at −78__C. then warmed to 0__C. whereupon 3N aqueous sodium hydroxide (35 mL) followed by 30% aqueous hydrogen peroxide (17.3 mL). Stirred at room temperature for two hours then evaporated the tetrahydrofuran. The residue was extracted with dichloromethane (3×75 mL). Dried the organic extracts over magnesium sulfate then evaporated. The residue was purified by preparative HPLC using silica gel eluting with 10% to 50% ethyl acetate in hexanes to yield [endo] 2-aza-2-benzylbicyclo[2.2.1]heptan-5-ol (23.5 mmol).

[endo] 2-Aza-2-(t-butoxycarbonyl)-5-((4-propylthio-1,2,5-thiadiazol-3-yl)oxy)bicyclo[2.2.1]heptane

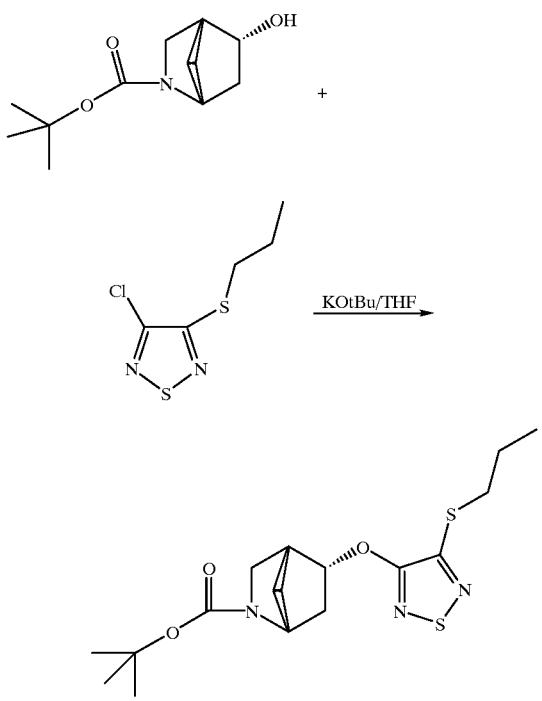

Potassium t-butoxide (23.5 mmol) was added to a solution of [endo] 2-aza-2-(t-butoxycarbonyl)-bicyclo[2.2.1]heptan-5-ol (23.5 mmol) in tetrahydrofuran (250 mL) at room temperature. Stirred for one hour whereupon the reaction was cooled to −10_C. and 3-chloro-4-propylthio-1,2,5-thiadiazole (28.2 mmol) in tetrahydrofuran (50 mL). The reaction was stirred at −10_C. for four hours then the reaction was poured into brine then extracted with ethyl acetate (3×200 mL). The combined organic extracts were washed with a saturated sodium chloride solution and dried over sodium sulfate, then evaporated. The residue was purified by preparative HPLC using silica gel eluting with 15 to 60% ethyl acetate in hexanes to yield [endo] 2-aza-2-(t-butylcarbonyl)-5-((4-propylthio-1,2,5-thiadiazol-3-yl)oxy)bicyclo[2.2.1]heptane (11.3 mmol).

EXAMPLE 27

[endo]2-Aza-5-((4-propylthio-1,2,5-thiadiazol-3-yl)oxy)bicyclo[2.2.1]heptane

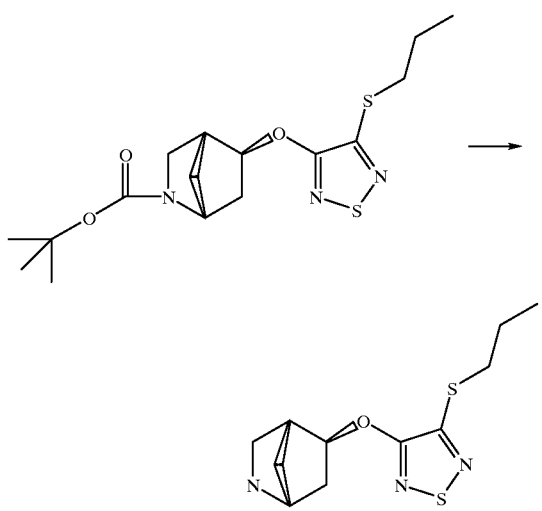

Trifluoroacetic acid (1.3 mL) was added to a solution of [endo]-2-aza-2-(t-butoxycarbonyl)-5-((4-propylthio-1,2,5-thiadiazol-3-yl)oxy)bicyclo[2.2.1]heptane (1.3 mmol) in methylene chloride (35 mL) at 0_C. The reaction was stirred at 0_C. for one hour then warmed to room temperature and stirred for sixteen hours. The reaction was concentrated on a rotary evaporator and the residue was basified with aqueous sodium bicarbonate then extracted with ethyl acetate (3×75 mL). The combined organic extracts were dried over magnesium sulfate then evaporated to yield [endo]-2-aza-5-((4-propylthio-1,2,5-thiadiazol-3-yl)oxy)bicyclo[2.2.1]heptane which was isolated as the hydrochloride salt to yield 201 mg of LY368586 (mp=82–86_C.).

EXAMPLE 28

Synthesis of 2-Aza-2-benzylbicyclo[2.2.1]hept-5-ene

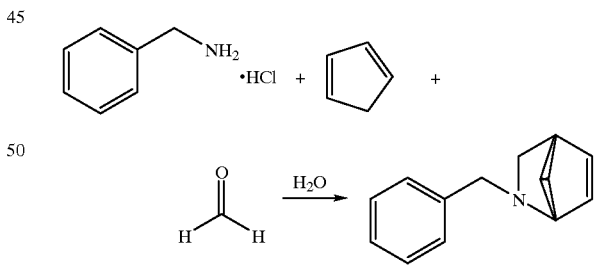

Cyclopentadiene (61.7 g/935 mmol) was added to a solution of benzylamine hydrochloride (67.1 g/467 mmol), 37% aqueous formaldehyde (65.4 mL/807 mmol), and water (190 mL). The solution was stirred at room temperature for three hours. Water (190 mL) was added to the reaction then washed with diethyl ether (2×250 mL). The aqueous layer was basified with solid KOH then extracted with diethyl ether (3×250 mL). The combined extracts were dried over magnesium sulfate then evaporated to yield 2-aza-2-benzylbicyclo[2.2.1]hept-5-ene (79.6 g/430 mmol)

Synthesis of [exo] 2-Aza-2-benzylbicyclo[2.2.1]heptan-5-ol and [exo] 2-Aza-2-benzylbicyclo[2.2.1]heptan-6-ol

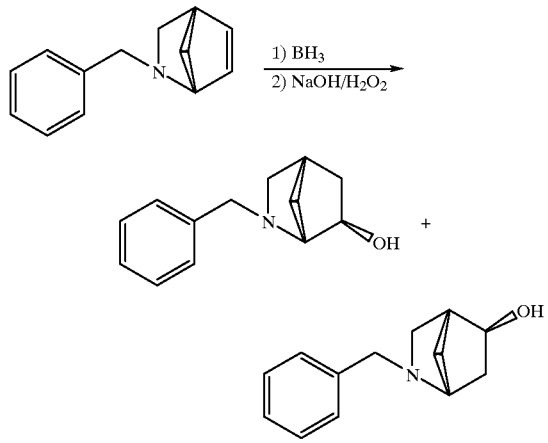

1.0M Borane:THF in tetrahydrofuran (500 mL/500 mmol) was added to a solution of 2-aza-2-benzylbicyclo[2.2.1]hept-5-ene (46.7 g/252.2 mmol) in tetrahydrofuran (570 mL) at 0_C. Stirred at 0_C. for 2 hours whereupon water in tetrahydrofuran was added to the reaction to destroy excess borane. While keeping the reaction temperature below 10_C., 3N Aqueous sodium hydroxide (30 mL) was added to the reaction immediately followed by 30% aqueous hydrogen peroxide (50 mL). The rection temperature was allowed to rise to 40_C then stirred for 1.5 hours. Postassium carbonate (10 g) was added to the reaction then evaporated to remove the tetrahydrofuran. The aqueous residue was extracted with dichloromethane (3×100 mL). The organic extracts were washed with water then dried over sodium chloride/sodium sulfate then evaporated. The residue was purified by preprative HPLC using silica gel eluting with 1 to 20% (10% ammonium hydroxide in methanol) in dichloromethane to yield [exo] 2-aza-2-benzylbicyclo[2.2.1]heptan-5-ol (7.2 g/36 mmol) and [exo] 2-aza-2-benzylbicyclo[2.2.1]heptan-6-ol (31.2 g/154 mmol).

Synthesis of [exo] 2-Aza-2-benzyl-6-((4-butoxy-1,2,5-thiadiazol-3-yl)oxy)bicyclo[2.2.1]heptane

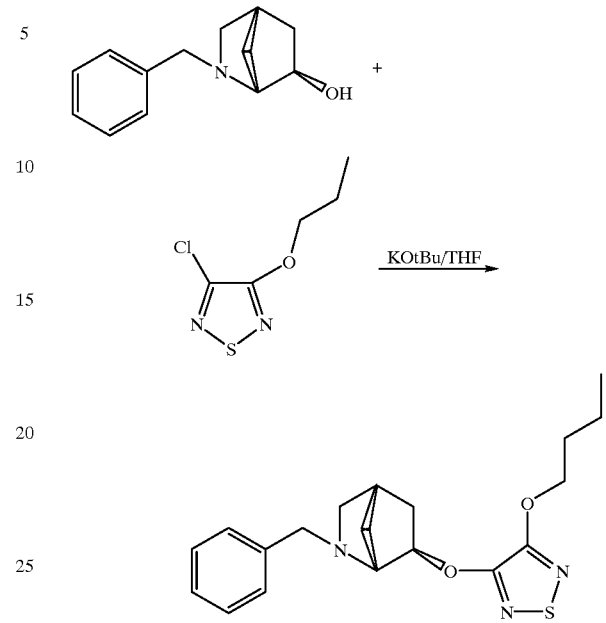

Potassium t-butoxide (0.66 g/5.9 mmol) was added to a solution of [exo] 2-aza-2-benzylbicyclo[2.2.1]heptan-6-ol (1.2 g/5.9 mmol) in tetrahydrofuran (50 mL) at −78_C. Stirred for 30 minutes where upon 3-chloro-4-butoxy-1,2,5-thiadiazole (1.1 g/5.9 mmol) in tetrahydrofuran (20 mL). The reaction was stirred at −78_C. for 16 hours then 1 hour at room temperature. The reaction was poured into brine then extracted with ethyl acetate (3×75 mL). The combined organic extracts were washed with brine, dried over magnesium sulfate, then evaporated. The residue was purified by flash chromatography on silica gel eluting with 20% ethyl acetate in hexanes to yield [exo] 2-aza-2-benzyl-6-((4-butoxy-1,2,5-thiadiazol-3-yl)oxy)bicyclo[2.2.1]heptane (0.4 g/1.1 mmol).

EXAMPLE 29

Synthesis of [exo] 2-Aza-6-((4-butoxy-1,2,5-thiadiazol-3-yl)oxy)bicyclo[2.2.1]heptane

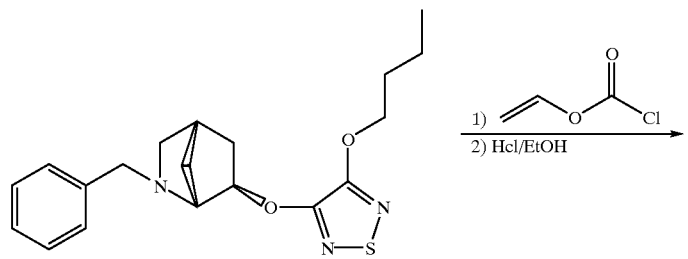

-continued

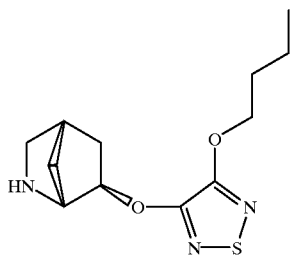

Vinyl chloroformate (2.2 mL/25.8 mmol) was added to a solution of [exo] 2-aza-2-benzyl-6-((4-butoxy-1,2,5-thiadiazol-3-yl)oxy)bicyclo[2.2.1]heptane (0.7 g/1.9 mmol), proton sponge (0.8 g/3.8 mmol), and dichloromethane (50 mL). The reaction was refluxed for 16 hours. The reaction was diluted with diethyl ether (110 mL) then washed with 1N aqueous hydrochloric acid (3×20 mL), saturated aqueous sodium bicarbonate (20 mL), and brine (20 mL). The organic layer was dried over magnesium sulfate then evaporated. The residue was taken up in ethanol (15 mL) and ethanol saturated with hydrochloric acid (15 mL) then refluxed for 6 hours. The solution was evaporated, basified with saturated aqueous sodium bicarbonate, then extracted with ethyl acetate (3×50 mL). The organic extracts were washed with a saturated sodium chloride solution and dried over sodium sulfate then evaporated. The residue was purified by radial chromatography on silica gel eluting with 1% conc. ammonium hydroxide/10% ethanol in chloroform to yield [exo]-2-aza-6-((4-butoxy-1,2,5-thiadiazol-3-yl)oxy) bicyclo[2.2.1]heptane which was isolated as the oxalate salt to yield 250 mg of LY335838 (mp=165–167_C.).

The following compounds were made using substantially the same procedure.

[exo] 2-Aza-2-benzyl-6-((4-propyl thio-1,2,5-thiadiazol-3-yl)oxy)bicyclo[2.2.1]heptane oxalate, LY338901, mp 151–154_C.

[exo] 2-Aza-6-((4-propyl thio-1,2,5-thiadiazol-3-yl)oxy) bicyclo[2.2.1]heptane hydrochloride, LY338902, mp 167–70_C.

[exo] 2-Aza-5-((4-propyl thio-1,2,5-thiadiazol-3-yl)oxy) bicyclo[2.2.1]heptane oxalate, LY341211, mp 159–162_C.

[exo] 2-Aza-5-((4-butoxy-1,2,5-thiadiazol-3-yl)oxy) bicyclo[2.2.1]heptane oxlate, LY343125, mp 161–162_C.

[exo] 2-Aza-5-((4-propoxy-1,2,5-thiadiazol-3-yl)oxy) bicyclo[2.2.1]heptane hydrochloride, LY344087, mp 144–146_C.

EXAMPLE 30

Synthesis of 2-Aza-2-benzylbicyclo[2.2.1]heptan-6-one

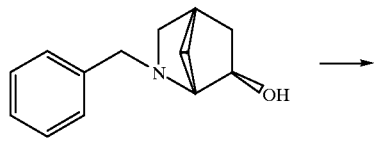

-continued

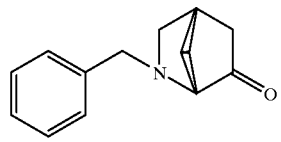

Dimethylsulfoxide (5.9 mL/82.9 mmol) was added to a solution of oxalyl chloride (3.3 mL/38.0 mmol) in dichloromethan (125 mL) at −78_C. Stirred for 20 minutes whereupon [exo]2-aza-2-benzylbicyclo[2.2.1]heptan-6-ol (7.0 g/34.5 mmol) in dichloromethane (15 mL). Stirred at −78_C. for 3 hours then triethylamine (24 mL/172.5 mmol) was added to the reaction then warmed to room temperature for 1 hour. Brine (75 mL) was added then the reaction was extracted with dichloromethane (3×100 mL). The organic extracts were dried over magnesium sulfate then evaporated. The residue was purified by flash chromatagraphy over silica gel eluting with ethyl acetate in hexanes to yield 2-aza-2-benzylbicyclo[2.2.1]heptan-6-one (3.5 g/17.4 mmol).

Synthesis of [endo] 2-Aza-2-benzylbicyclo[2.2.1] heptan-6-ol

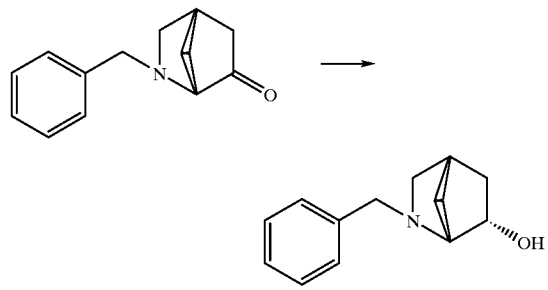

L-Selectride (44.1 mL/44.1 mmol) was added to a solution of 2-aza-2-benzylbicyclo[2.2.1]heptan-6-one (3.5 g/17.4 mmol) in tetrahydrofuran (90 mL) at −78_C. Stirred for 3 hours at −78_C. then warmed to 0_C. whereupon 3N aqueous sodium hydroxide (19 mL) followed by 30% aqueous hydrogen peroxide (9.5 mL). Stirred at room temperature for 2 hours then evaporated the tetrahydrofuran. The residue was extracted with dichloromethane (3×75 mL). Dried the organic extracts over magnesium sulfate then evaporated. The residue was purified by 1% ammonium hydroxide/9% methanol/40% chloroform/50% dichloromethane to yield [endo] 2-aza-2-benzylbicyclo[2.2.1] heptan-6-ol (3 g/14.8 mmol)

43

Synthesis of [endo] 2-Aza-2-benzyl-6-((4-propylthio-1,2,5-thiadiazol-3-yl)oxy)bicyclo[2.2.1]heptane

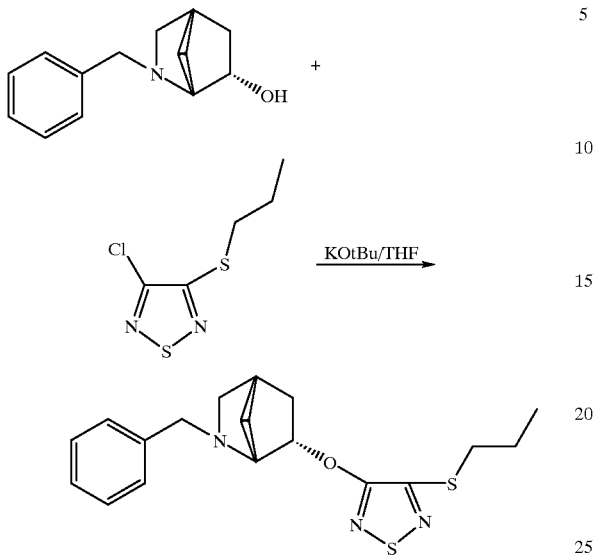

Potassium t-butoxide (1.7 g/14.8 mmol) was added to a solution of [endo] 2-aza-2-benzylbicyclo[2.2.1]heptan-6-ol (3.0 g/14.8 mmol) in tetrahydrofuran (150 mL) at room temperature. Stirred for 45 minutes where upon 3-chloro-4-propylthio-1,2,5-thiadiazole (2.8 g/14.5 mmol) in tetrahydrofuran (25 mL). The reaction was stirred at room temperature for 16 hours then 1 hour at room temperature. The reaction was poured into brine then extracted with ethyl acetate (3×75 mL). The combined organic extracts were washed with brine, dried over magnesium sulfate, then evaporated. The residue was purified by flash chromatagraphy on silica gel eluting with 20% ethyl acetate in hexanes to yield [endo] 2-aza-2-benzyl-6-((4-propylthio-1,2,5-thiadiazol-3-yl)oxy)bicyclo[2.2.1]heptane (0.9 g/2.5 mmol).

EXAMPLE 31

Synthesis of [endo] 2-Aza-6-((4-propylthio-1,2,5-thiadiazol-3-yl)oxy)bicyclo[2.2.1]heptane

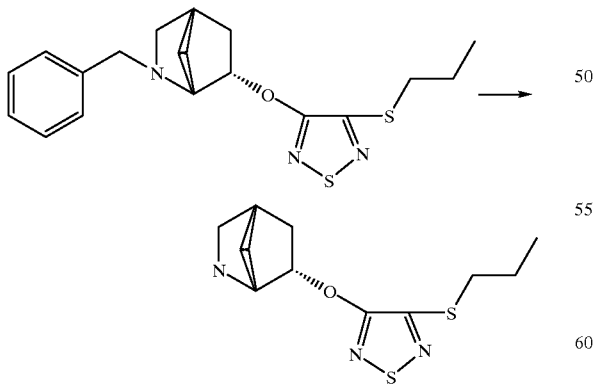

Vinyl chloroformate (0.6 mL/6.6 mmol) was added to a solution of [endo] 2-aza-2-benzyl-6-(4-propylthio-1,2,5-thiadiazol-3-yl)oxy)bicyclo[2.2.1]heptane (0.8 g/2.2 mmol), proton sponge (0.9 g/4.4 mmol), and dichloromethane (40 mL). The reaction was refluxed for 16 hours. The reaction was diluted with diethyl ether (100 mL) then washed with 1N aqueous hydrochloric acid (3×20 mL), saturated aqueous sodium bicarbonate (20 mL), and brine (20 mL). The organic layer was dried over magnesium sulfate then evaporated. The residue was taken up in ethanol (15 mL) and ethanol saturated with hydrochloric acid (15 mL) then refluxed for 6 hours. The solution was evaporated, basified with saturated aqueous sodium bicarbonate, then extracted with ethyl acetate (3×50 mL). The organic extracts were washed with a saturated sodium chloride solution and dried over sodium sulfate then evaporated. The residue was purified by radial chromatagraphy on silica gel eluting with 0.5% conc. ammonium hydroxide/5% ethanol in chloroform to yield [endo]-2-aza-6-((4-propylthio-1,2,5-thiadiazol-3-yl)oxy)bicyclo[2.2.1]heptane which was isolated as the hydrochloride salt to yield 130 mg of LY338903 (mp=163–164_ C.).

EXAMPLE 32

Synthesis of [exo] 2-Aza-2-benzyl-6-((4-propylsulfonyl-1,2,5-thiadiazol-3-yl)oxy)bicyclo[2.2.1]heptane

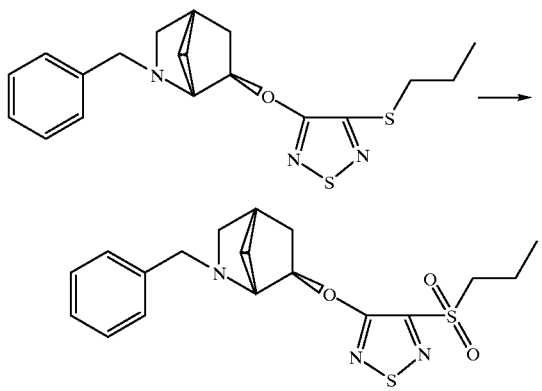

A solution of Oxone® (36.9 g/60.1 mmol) in water (75 mL) was added to a solution of [exo] 2-Aza-2-benzyl-6-((4-propylthio-1,2,5-thiadiazol-3-yloxy)bicyclo[2.2.1]heptane (10.7 g/29.6 mmol), 1N aqueous hydrochloric acid (30 mL), water (75 mL), and tetrahydrofuran (75 mL). Stirred at room temperature for 16 hours. Saturated aqueous sodium bisulfite was added to the reaction which was extracted with diethyl ether (3×200 mL). The organic extracts were washed with water, saturated aqueous sodium bicarbonate, water, dried over magnesium sulfate, then evaporated to yield [exo] 2-Aza-2-benzyl-6-((4-propylsulfonyl-1,2,5-thiadiazol-3-yl)oxy)bicyclo[2.2.1]heptane (12 g).

EXAMPLE 33

Synthesis of [exo] 2-Aza-2-benzyl-6-((4-(4,4,4-trifluorobutoxy)-1,2,5-thiadiazol-3-yl)oxy)bicyclo[2.2.1]heptane

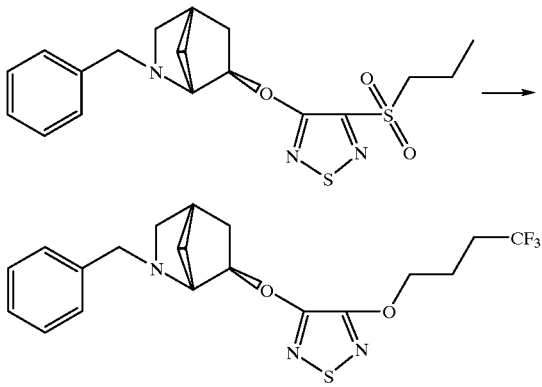

4,4,4-Trifluorobutanol (2.0 g/15.3 mmol) was added to a mixture of sodium hydride (14.0 mmol) and tetrahydrofuran (40 mL). The reaction was stirred for 1 hour at room temperature. [exo] 2-Aza-2-benzyl-6-((4-propylsulfonyl-1,2,5-thiadiazol-3-yl)oxy)bicyclo[2.2.1]heptane (2.0 g/5.1 mmol) in tetrahydrofuran (10 mL) was added to the reaction. The reaction was stirred for 16 hours then evaporated. The residue was taken up in water and extracted with ethyl acetate (3×100 mL). The extracts were dried over sodium chloride/sodium sulfate then evaporated. The residue was purified by flash chromatography over silica gel eluting with 25% ethyl acetate in hexanes to yield [exo] 2-Aza-2-benzyl-6-((4-(4,4,4-trifluorobutoxy)-1,2,5-thiadiazol-3-yl)oxy)bicyclo[2.2.1]heptane (1.1 g/2.7 mmol).

EXAMPLE 34

Synthesis of [exo] 2-Aza-6-((4-(4,4,4-trifluorobutoxy)-1,2,5-thiadiazol-3-yl)oxy)bicyclo[2.2.1]heptane

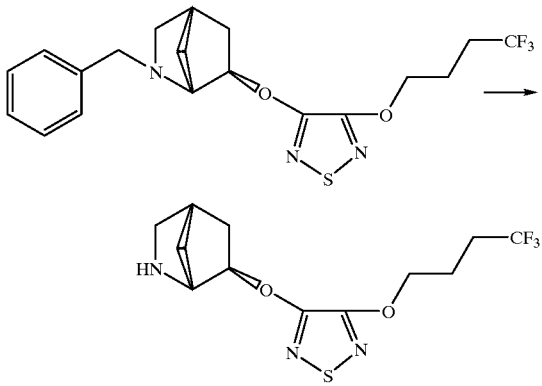

Vinyl chloroformate (0.8 mL/9.3 mmol) was added to a solution of [exo] 2-Aza-2-benzyl-6-((4-(4,4,4-trifluorobutoxy)-1,2,5-thiadiazol-3-yl)oxy)bicyclo[2.2.1]heptane (1.5 g/3.1 mmol), proton sponge (1.3 g/6.2 mmol), and dichloromethane (100 mL). The reaction was refluxed for 16 hours. The reaction was diluted with diethyl ether (500 mL) then washed with 1N aqueous hydrochloric acid (3×80 mL), saturated aqueous sodium bicarbonate (80 mL), and brine (80 mL). The organic layer was dried over magnesium sulfate then evaporated. The residue was taken up in ethanol (60 mL) and ethanol saturated with hydrochloric acid (60 mL) then refluxed for 6 hours. The solution was evaporated, basified with saturated aqueous sodium bicarbonate, then extracted with ethyl acetate (3×50 mL). The organic extracts washed with a saturated sodium chloride solution and were dried over sodium sulfate then evaporated. The residue was purified by radial chromatography on silica gel eluting with 1% conc. ammonium hydroxide/10% ethanol in chloroform to yield [exo] 2-Aza-6-((4-(4,4,4-trifluorobutoxy)-1,2,5-thiadiazol-3-yl)oxy)bicyclo[2.2.1]heptane which was isolated as the hydrochloride salt to yield 130 mg of LY343953 (mp=128–130_C.).

The following compounds were made using substantially the same procedure.

[exo] 2-Aza-6-((4-(4-(trifluoromethoxy)benzyloxy)-1,2,5-thiadiazol-3-yl)oxy)bicyclo[2.2.1]heptane hydrochloride, LY343954, mp 147–149_C.

[exo] 2-Aza-6-((4-propoxy-1,2,5-thiadiazol-3-yl)oxy)bicyclo[2.2.1]heptane hydrochloride, LY343955, mp 173–174_C.

[exo] 2-Aza-6-((4-ethyloxy-1,2,5-thiadiazol-3-yl)oxy)bicyclo[2.2.1]heptane hydrochloride, LY344032, mp 177–179_C.

EXAMPLE 35

Synthesis of [exo] 2-Aza-bicyclo[2.2.1]heptan-6-ol

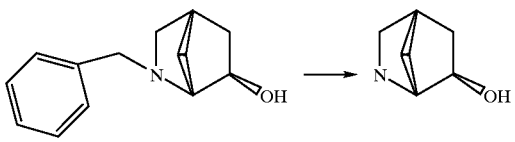

A solution of [exo] 2-aza-2-benzylbicyclo[2.2.1]heptan-6-ol (23.1 g/113.8 mmol) in ethanol (470 mL) was hydrogenated with 5% Pd/C (7 g) at 60 PSIG of hydrogen ato room temperature for 16 hours. Filtered off the catalyst the evaporated the filtrate. Isolated as the hydrochloride salt to yield [exo] 2-azabicyclo[2.2.1]heptan-6-ol hydrochloride (13 g).

Synthesis of [exo] 2-Aza-6-(4-hexoxy-1,2,5-thiadiazol-3-yloxy)bicyclo[2.2.1]heptane

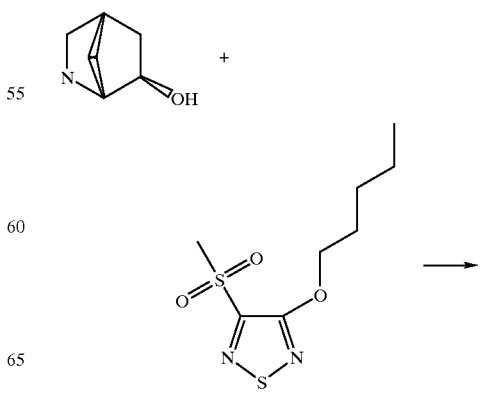

-continued

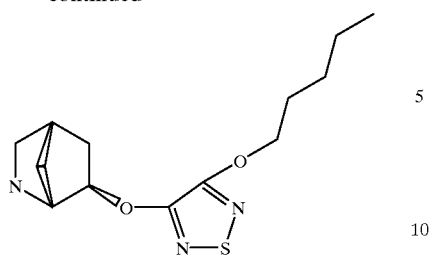

1.6M n-Butyllithium in hexanes (8.4 mL/13.4 mmol) was added to a solution of [exo] 2-azabicyclo[2.2.1]heptan-6-ol hydrochloride (1.0 g/6.7 mmol) in tetrahydrofuran (80 mL) at room temperature. Stirred for 1 hour then added 3-(methanesulfonyl)-4-hexyloxy-1,2,5-thiadiazole (2.0 g/8.0 mmol) in tetrahydrofuran (20 mL). Stirred at room temperature for 16 hours. Quenched the reaction with water then extracted with ethyl acetate (3×100 mL). The organic extracts were evaporated then taken up in 1N aqueous hydrochloric acid. The aqueous layer was washed with diethyl ether (2×50 mL) the basified with potassium carbonate then extracted the ethyl acetate (3×75 mL). The organic extracts were dried over magnesium sulfate then evaporated. The residue was treated with hydrochloric acid in diethyl ether to yield [exo] 2-Aza-6-(4-hexoxy-1,2,5-thiadiazol-3-yl) oxy)bicyclo [2.2.1]heptane hydrochloride, LY341711 (mp=131–134_C.)

EXAMPLE 36

Synthesis of 2-Aza-2-(t-butoxycarbonyl)-bicyclo [2.2.1]hept-5-ene

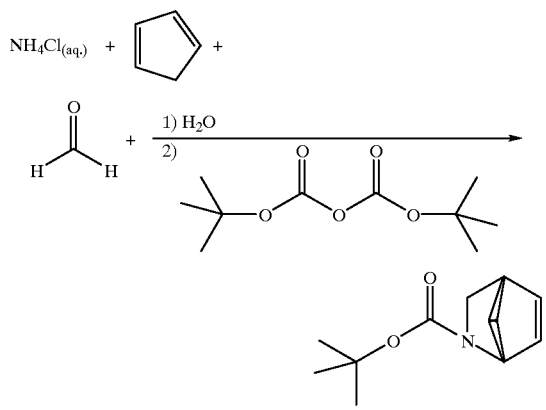

Cyclopentadiene (79 g/1.20 mol) was added to a solution of saturated aqueous ammonium chloride (257 mL) and 37% aqueous formaldehyde (68.1 mL/0.84 mol). The solution was stirred at room temperature for 16 hours. Water (130 mL) was added to the reaction then washed with diethyl ether (2×150 mL). The aqueous layer was basified with solid KOH. Di-t-butyldicarbonate (218 g/1.00 mol) was added to the aqueous layer while maintaining the pH between 9.5 and 10. Stirred overnight at room temperature. The reaction was extracted with ethyl acetate (3×500 mL). The combined extracts were washed with a saturated sodium chloride solution and dried over sodium sulfate then evaporated. The residue was purfied by preprative HPLC over silica gel eluting with 25 to 75% ethyl acetate in hexanes to yield 2-aza-2-(t-butoxycarbonyl)-bicyclo[2.2.1]hept-5-ene (62 g/318 mmol).

Synthesis of [exo] 2-Aza-2-(t-butoxycarbonyl)-bicyclo[2.2.1]heptan-5-ol and [exo] 2-Aza-2-(t-butoxycarbonyl)-bicyclo[2.2.1]heptan-6-ol

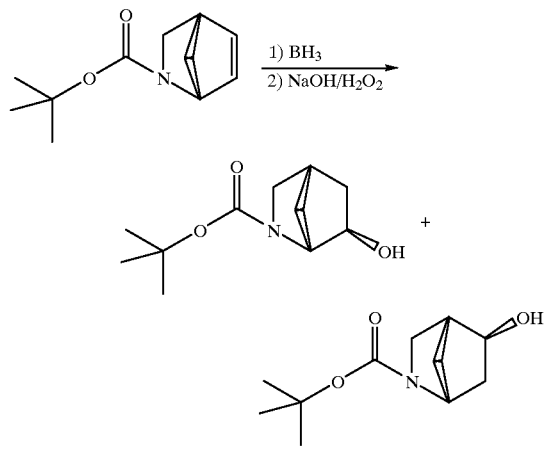

1.0 M Borane:THF in tetrahydrofuran (626 mL/626 mmol) was added to a solution of 2-aza-2-(t-butoxycarbonyl)-bicyclo[2.2.1]hept-5-ene (61.5 g/315 mmol) in tetrahydrofuran (700 mL) at 0_C. Stirred at 0_C. for 2 hours whereupon water in tetrahydrofuran was added to the reaction to destroy excess borane. While keeping the reaction temperature below 10_C., 3N Aqueous sodium hydroxide (88 mL) was added to the reaction immediately followed by 30% aqueous hydrogen peroxide (148 mL). The rection temperature was allowed to rise to 40_C. then stirred for 1.5 hours. Postassium carbonate (30 g) was added to the reaction then evaporated to remove the tetrahydrofuran. The aqueous residue was extracted with dichloromethane. The organic extracts were washed with a saturated sodium chloride and then dried over sodium sulfate then evaporated. The residue was purified by preprative HPLC using silica gel eluting with 10 to 75% ethyl acetate in hexanes to yield [exo] 2-aza-2-(t-butoxycarbonyl)-bicyclo[2.2.1]heptan-5-ol (14.0 g/65.7 mmol) and [exo] 2-aza-2-(t-butoxycarbonyl)-bicyclo[2.2.1]heptan-6-ol (14.5 g/68.1 mmol).

Synthesis of [exo] 2-Aza-2-t-butoxycarbonyl)-6-((4-propylthio-1,2,5-thiadiazol-3-yl)oxy)bicyclo[2.2.1] heptane

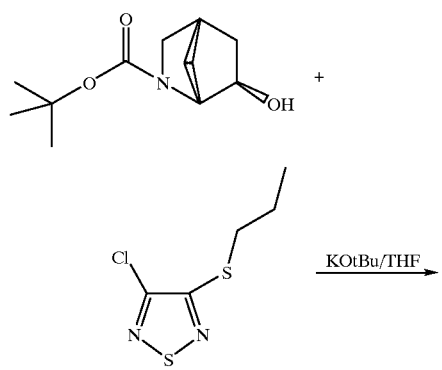

-continued

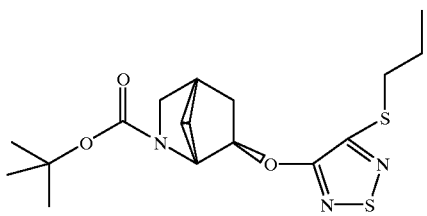

Potassium t-butoxide (2.6 g/23.5 mmol) was added to a solution of [exo] 2-aza-2-(t-butoxycarbonyl)-bicyclo[2.2.1]heptan-6-ol (5.0 g/23.5 mmol) in tetrahydrofuran (250 mL) at room temperature. Stirred for 2 hours whereupon the reaction was cooled to −10_C. and 3-chloro-4-propylthio-1,2,5-thiadiazole (4.6 g/23.5 mmol) in tetrahydrofuran (50 mL). The reaction was stirred at −10_C. for 1 hour then the reaction was poured into brine then extracted with ethyl acetate (3×250 mL). The combined organic extracts were washed with a saturated sodium chloride solution and dried over sodium sulfate, then evaporated. The residue was purified by prepative HPLC using silica gel eluting with 5 to 50% ethyl acetate in hexanes to yield [exo] 2-aza-2-(t-butylcarbonyl)-6-((4-propylthio-1,2,5-thiadiazol-3-yl)oxy)bicyclo[2.2.1]heptane (3.5 g/9.4 mmol).

EXAMPLE 37

Synthesis of [exo] 2-Aza-6-((4-propylsulfonyl-1,2, 5-thiadiazol-3-yl)oxy)bicyclo[2.2.1]heptane

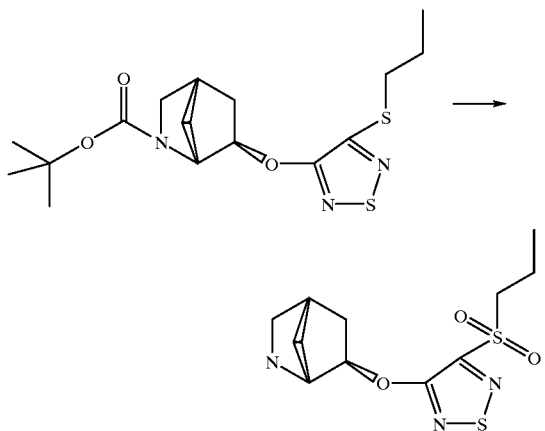

A solution of Oxone® (11.7 g/9.4 mmol) in water (40 mL) was added to a solution of [exo] 2-aza-2-(t-butoxycarbonyl)-6-((4-propylthio-1,2,5-thiadiazol-3-yl)oxy)bicyclo[2.2.1]heptane (3.5 g/9.4 mmol), 1N aqueous hydrochloric acid (10 mL), water (10 mL), and tetrahydrofuran (50 mL). Stirred at room temperature for 16 hours. Saturated aqueous sodium bisulfite was added to the reaction which was extracted with ethyl acetate (3×100 mL). The organic extracts were dried over sodium chloride/sodium sulfate, then evaporated. The residue was taken up in dichloromethane (10 mL) then was treated with trifluoroacetic acid (5 mL) at room temperature. Stirred for 2 hours the evaporated. The residue was taken up in saturated aqueous sodium bicarbonate then extracted with ethyl acetate (3×50 mL). The organic extracts were washed with a saturated sodium chloride solution and dried over sodium sulfate then evaporated to yield [exo] 2-Aza-6-((4-propylsulfonyl-1,2,5-thiadiazol-3-yloxy)bicyclo[2.2.1]heptane (2.2 g).

Synthesis of [exo] 2-Aza-6-((4-(3,3,3-trifluoropropoxy)-1,2,5-thiadiazol-3-yl)oxy)bicyclo[2.2.1]heptane

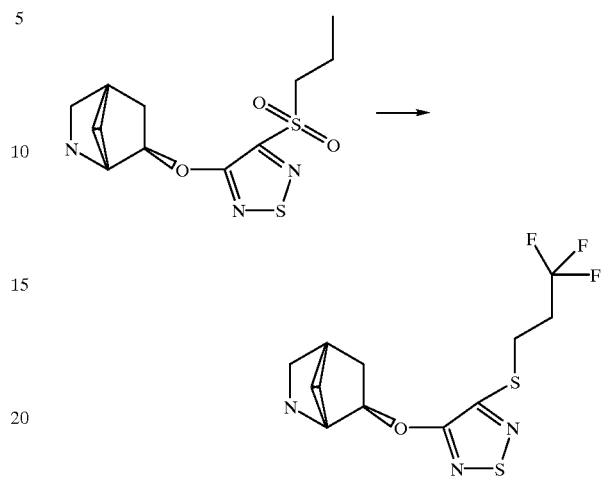

3,3,3-Trifluoropropanol (570 mg/1.7 mmol) was added to a mixture of postassium t-butoxide (560 mg/5.0 mmol) and tetrahydrofuran (15 mL). The reaction was stirred for 30 minutes at room temperature then cooled to −10_C. [exo] 2-Aza-6-((4-propylsulfonyl-1,2,5-thiadiazyl-3-oxy)bicyclo [2.2.1]heptane (500 mg/1.7 mmol) in tetrahydrofuran (5 mL) was added to the reaction. The reaction was stirred for 1.5 hours. The reaction was quenched with brine and extracted with ethyl acetate (3×75 mL). The extracts were washed with a saturated sodium chloride solution and dried over sodium sulfate then evaporated. The residue was purified by radial chromatagraphy over silica gel eluting with 1% conc. ammonium hydroxide/10% ethanol in chloroform to yield [exo] 2-Aza-6-((4-(3,3,3-trifluoropropoxy)-1,2,5-thiadiazol-3-yl)oxy)bicyclo[2.2.1]heptane (158 mg/0.51 mmol) which was isolated as the hydorchloride salt, LY344390 (mp=150–153_C.).

The following compounds were made using substantially the same procedure.

[exo] 2-Aza-6-((4-methoxy-1,2,5-thiadiazol-3-yl)oxy)bicyclo[2.2.1]heptane hydrochloride, LY344790, mp 180–182_C.

EXAMPLE 40

2-Methoxycarbonyl-2-aza-[2.2.1]-bicycloheptan-6-ol

A three-neck round-bottom flask fitted with two addition funnels was charged with NH$_4$Cl (146 g, 2.7 Mol), 37% aq. formaldehyde (110 mL, 1.4 Mol) and H$_2$O (500 mL) cyclopentadiene (60 g, 0.9 Mol) was added, and reaction was stirred at room temperature under an atmosphere of N$_2$. After 6 h, K$_2$CO$_3$ (40 g, 0.30 Mol) was added. Reaction cooled in an ice bath. One addition funnel was charged with methyl chloroformate (70 mL, 0.9 Mol) and the second addition funnel was charged with K$_2$CO$_3$ (125 g, 0.9 Mol) in H$_2$O (500 mL). The reagents from the two addition funnels were added dropwise at such a rate that K$_2$CO$_3$ completed just after methyl chloroformate, over a 30 min period. The reaction was then stirred for 2 h, with ice bath cooling. The reaction was then extracted with three 500 mL portions of CH$_2$Cl$_2$. The combined extracts were washed with a saturated sodium chloride solution and dried over sodium sulfate and evaporated under vacuum. Chromatography of 10 g of the resulting brown oil (1:1 ethyl acetate, hexanes) afforded 4.3 g of a colorless oil.

A solution of the product (4.3 g, 28 mMol) in 60 mL of dry THF, under an $N_2$ atmosphere was cooled in an ice bath. $BH_3$.THF (57 mL, 57 mMol) was added and the reaction was stirred for 2 h with continued ice bath cooling. The reaction was then quenched by addition of a mixture of 5 mL $H_2O$ combined with 5 mL THF, followed by 10 mL of 5 N NaOH and careful addition of 10 mL 30% $H_2O_2$. The resulting mixture was stirred vigorously for 1.5 h. The mixture was then concentrated under vacuum to remove THF. The residue was diluted with 50 mL brine and extracted with three 50 mL portions of $CH_2Cl_2$. The combined extracts were washed with a saturated soduim chloride solution and dried over sodium sulfate and evaporated. Chromatography (ethyl acetate) afforded 2.8 g of the title compound.

EXAMPLE 41

Synthesis of [exo] 2-Aza-2-(methoxycarbonyl)-6-((4-(ethylthio)-1,2,5-thiadiazol-3-yl)oxy)bicyclo[2.2.1]heptane

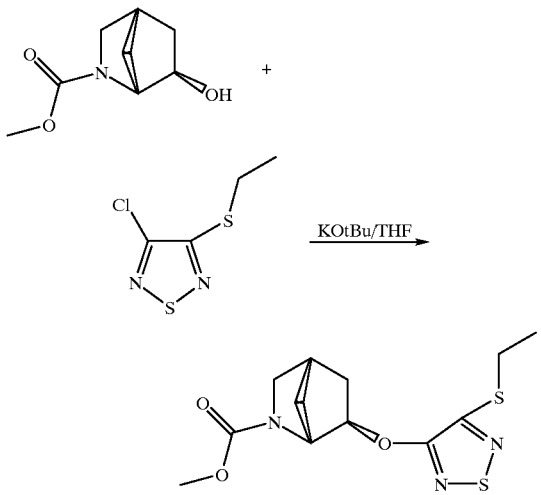

Postassium t-butoxide (0.65 g/5.8 mmol) was added to a solution of [exo] 2-aza-2-(methoxycarbonyl)bicyclo[2.2.1]heptan6-ol (1.0 g/5.8 mmol) in tetrahydrofuran (50 mL). Stirred at room temperature for 45 minutes whereupon 3-chloro-4-(ethylthio)-1,2,5-thiadiazole (0.95 g/5.3 mmol) was added to the reaction. Stirred overnight at room temperature. Poured the reaction into brine and extracted with ethyl acetate (3×75 mL). The organic extracts were dried over magnesium sulfate then evaporated. The residue was purified by radial chromatagraphy on silica gel eluting with 25% ethyl acetate in hexanes to yield [exo] 2-aza-2-(methoxycarbonyl)-6-((4-(ethylthio)-1,2,5-thiadiazol-3-yl)oxy)bicyclo[2.2.1]heptane (500 mg/1.7 mmol).

EXAMPLE 42

Synthesis of [exo] 2-Aza-6-((4-(ethylthio)-1,2,5-thiadiazol-3-yl)oxy)bicyclo[2.2.1]heptane

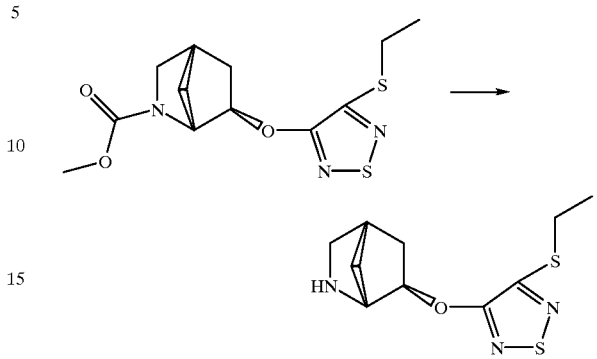

Trimethylsilyl iodide (0.4 mL/2.0 mmol) was added to a solution of [exo] 2-aza-2-(methoxycarbonyl)-6-(4-(ethylthio)-1,2,5-thiadiazyl-3-oxy)bicyclo[2.2.1]heptane (500 mg/1.7 mmol) in dichloromethane (25 mL). The reaction was refluxed for 16 hours. The reaction was poured into methanol then evaporated. The residue was purified by radial chromatagraphy over silica gel eluting with 0.5% conc. ammonium hydroxide/5.0% ethanol in chloroform to yield [exo] 2-Aza-6-((4-(ethylthio)-1,2,5-thiadiazol-3 -yl)oxy)bicyclo[2.2.1]heptane (145 mg/0.56 mmol) which was isolated as the oxalate salt, LY338327 (dec 182_C.).

The following compounds were made using substantially the same procedure.

[exo] 2-Aza-6-((4-butoxy-1,2,5-thiadiazol-3-yl)oxy)bicyclo[2.2.1]heptane oxlate, LY335838, mp 162–164_C.

[exo] 2-Aza-6-((4-hexoxy-1,2,5-thiadiazol-3-yl)oxy)bicyclo[2.2.1]heptane oxlate, LY333582, mp 171–173_C.

EXAMPLE 43

To a solution of an alcohol or an aliphatic thiol (0.5 mmol, 2 equiv.) in 4.0 mL of anhydrous THF contained in a 8 mL vial was added 1 mL of a 0.5 M mixture of potassium tert-butoxide (0.5 mmol, 2 equiv.) in THF. The vial was capped, briefly shaken and then cooled to around 0_C in an aluminum block. The vial was uncapped, a solution of sulfone (0.25 mmol, 1 equiv.) in THF was quickly added and then the vial was immediately recapped. The reaction mixture was shaken at ambient temperature overnight and was then added directly to 12 mL of a 30% solution of TFA in chloroform. After shaking overnight and concentrated under vacuum, the resulting residue was placed overnight in a vacuum oven with light heating (50° C). The residue was then re dissolved in a 15% solution of methanol in chloroform and passed through a Varion SAX ion exchange column (1 g, 6 mL column) which had been pretreated by washing with 1 N NaOH (20 mL) and methanol (8 mL). The resulting filtrate (total volume 12 mL) was then passed through a Varion SCX ion exchange column (1 g, 3 mL column). The column was washed 3–4× with 3.0 mL portions of MeOH and the product eluted from the column using four 2 mL portions (8 mL total) of a 20% solution of sat. HCl.MeOH (or sat. HCl ethanol)/$CHCl_3$. Concentration in a speed vac provided the hydrochloride salts of the products which were submitted for testing without further purification.

The following compounds were prepared using the same procedure as described above by using the appropriate starting materials.

(1R,4S,6R)-2-Aza-((4-(2-(4-chlorophenyl)-2-cyclopentylethoxy)-1,2,5-thiadiazol-3-yl)oxy)bicyclo[2.2.1]heptane hydrochloride, LY362818, MW=442.4 g/mol, MF=C20 H25 Cl2 N3 O2 S, m/z+1=406.2,408.2.

(1R,4S,6R)-2-Aza-((4-(4-chlorobenzyl)thio)-1,2,5-thiadiazol-3-yl)oxy)bicyclo[2.2.1]heptane hydrochloride, LY362819, MW=390.5 g/mol, MF=C15 H17 Cl2 N3 O S2, m/z+1=354.

(1R,4S,6R)-2-Aza-((4-(3-(4-fluorophenyl)propoxy)-1,2,5-thiadiazol-3-yl)oxy)bicyclo[2.2.1]heptane hydrochloride, LY362820, MW=385.9 g/mol, MF=C17 H21 Cl F N3 O S2, m/z+1=350.1.

(1R,4S,6R)-2-Aza-((4-(3-phenyl)prop-2-ynyloxy)-1,2,5-thiadiazol-3-yl)oxy)bicyclo[2.2.1]heptane hydrochloride, LY362821, MW=363.9 g/mol, MF=C17 H18 Cl N3 O2 S, m/z+1=328.3.

(1R,4S,6R)-2-Aza-((4-(hexyloxy-1,2,5-thiadiazol-3-yl)oxy)bicyclo[2.2.1]heptane hydrochloride, LY362822, MW=333.9 g/mol, MF=C14 H24 Cl N3 O2 S, m/z+1=298.3.

(1R,4S,6R)-2-Aza-((4-but-2-ynyloxy-1,2,5-thiadiazol-3-yl)oxy)bicyclo[2.2.1]heptane hydrochloride, LY362823, MW=301.8 g/mol, MF=C12 H16 Cl N3 O2 S, m/z+1=266.4.

(1R,4S,6R)-2-Aza-((4-(2-cycloproylethoxy)-1,2,5-thiadiazol-3-yl)oxy)bicyclo[2.2.1]heptane hydrochloride, LY362824, MW=303.8 g/mol, MF=C12 H17 Cl N3 O2 S, m/z+1=268.

(1R,4S,6R)-2-Aza-((4-(4-fluorobenzyl)thio)-1,2,5-thiadiazol-3-yl)oxy)bicyclo[2.2.1]heptane hydrochloride, LY362826, MW=357.8 g/mol, MF=C15 H17 Cl F N3 O2 S, m/z+1=322.5.

(1S,4R,6S)-2-Aza-((4-(2-cyclohexyl-cyclohexoxy)-1,2,5-thiadiazol-3-yl)oxy)bicyclo[2.2.1]heptane hydrochloride, LY368363, MW=414.0 g/mol, MF=C20 H32 Cl N3 O2 S, m/z+1=378.2.

(1S,4R,6S)-2-Aza-((4-(4-phenylbenzyloxy)-1,2,5-thiadiazol-3-yl)oxy)bicyclo[2.2.1]heptane hydrochloride, LY368364, MW=415.9 g/mol, MF=C21 H22 Cl N3 O2 S, m/z+1=380.1.

(1S,4R,6S)-2-Aza-((4-(2-(4-chlorophenylthio)ethyoxy)-1,2,5-thiadiazol-3-yl)oxy)bicyclo[2.2.1]heptane hydrochloride, LY368365, MW=420.4 g/mol, MF=C16 H19 Cl N3 O2 S2, m/z+1=384.1.

(1S,4R,6S)-2-Aza-((4-(2-phenyl-2-cyclopropylethoxy)-1,2,5-thiadiazol-3-yl)oxy)bicyclo[2.2.1]heptane hydrochloride, LY368366, MW=379.9 g/mol, MF=C18 H22 Cl N3 O2 S, m/z+1=344.

(1S,4R,6S)-2-Aza-((4-(3-(benzyloxy)propoxy)-1,2,5-thiadiazol-3-yl)oxy)bicyclo[2.2.1]heptane hydrochloride, LY368367, MW=397.9 g/mol, MF=C18 H24 Cl N3 O3 S, m/z+1=362.1.

(1S,4R,6S)-2-Aza-((4-(2-diphenyethoxy)-1,2,5-thiadiazol-3-yl)oxy)bicyclo[2.2.1]heptane hydrochloride, LY368368, MW=429.9 g/mol, MF=C22 H24 Cl N3 O2 S, m/z+1=394.1.

(1S,4R,6S)-2-Aza-((4-(1-(2-thienyl)-2-propoxy)-1,2,5-thiadiazol-3-yl)oxy)bicyclo[2.2.1]heptane hydrochloride, LY368370, MW=373.9 g/mol, MF=C15 H20 Cl N3 O2 S2, m/z+1=338.1.

(1S,4R,6S)-2-Aza-((4-(2-phenyl-2-cyclopentylethoxy)-1,2,5-thiadiazol-3-yl)oxy)bicyclo[2.2.1]heptane hydrochloride, LY368371, MW=421.9 g/mol, MF=C21 H28 Cl N3 O2 S, m/z+1=386.2.

(1S,4R,6S)-2-Aza-((4-(3-(methylthio)-1-hexoxy)-1,2,5-thiadiazol-3-yl)oxy)bicyclo[2.2.1]heptane hydrochloride, LY368374, MW=379.9 g/mol, MF=C15 H26 Cl N3 O2 S2, m/z+1=344.

(1S,4R,6S)-2-Aza-((4-(2,3-pentafluoro-1-propoxy)-1,2,5-thiadiazol-3-yl)oxy)bicyclo[2.2.1]heptane hydrochloride, LY368376, MW=381.8 g/mol, MF=C11 H13 Cl F5 N3 O2 S, m/z+1=346.1.

EXAMPLE 44

Preparation

[exo] 2-Aza-2-benzylcarbonyl-bicyclo[2.2.1]heptan-6-ol

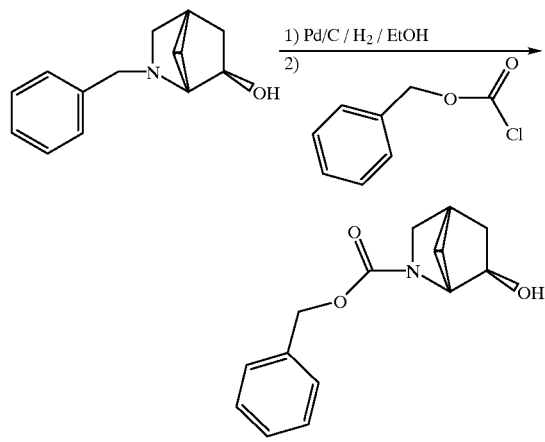

A solution of 2-benzyl-2-azabicyclo[2.2.1]heptan-6-ol (5.0 mmol) in ethanol (75 mL) and ethyl acetate (75 mL) was hydrogenated with 5% Pd/C (10 g) at 60 PSIG of hydrogen at room temperature for 16 hours. The catalyst was filtered off and the filtrate was evaporated. A solution of the filtrate in tetrahydrofuran (100 mL) and H$_2$O (50 mL) was cooled to 0__C. The pH was adjusted to 10 with 5N aqueous sodium hydroxide. Benzylchloroformate (5.1 mmol) was added to the reaction solution while the pH was maintained between 9 and 10 with 5N aqueous sodium hydroxide. The reaction was stirred at 0__C. for three hours, poured into ethyl acetate, washed with 1N HCl(aq), dried over sodium sulfate, then evaporated to yield [exo] 2-aza-2-(benzylcarbonyl)-bicyclo[2.2.1]heptan-6-ol (4.9 mmol).

[exo] 2-Aza-2-benzylcarbonyl-6-((4-(propylthio)-1,2,5-thiadiazol-3-yl)oxy)bicyclo[2.2.1]heptane

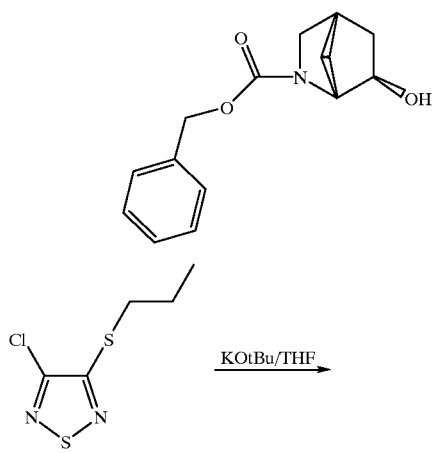

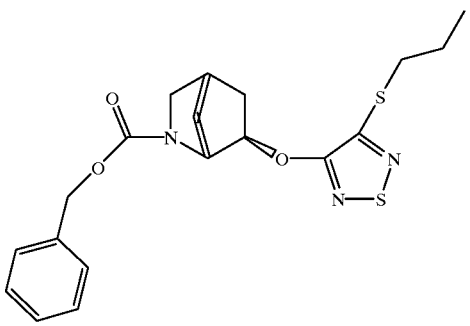

Potassium t-butoxide (2.6 mmol) was added to a solution of [exo] 2-aza-2-benzylcarbonyl-bicyclo[2.2.1]heptan-6-ol (2.6 mmol) in tetrahydrofuran (250 mL). Stirred at –10_C for 30 minutes whereupon 3-chloro-4-(propylthio)-1,2,5-thiadiazole (2.6 mmol) in tetrahydrofuran (50 mL) was added to the reaction. Stirred for two hours at –10_C. then room temperature for sixteen hours. The reaction mixture was poured into water and extracted with ethyl acetate. The organic extracts were dried and evaporated. The residue was purified by preparative HPLC using silica gel eluting with 30% ethyl acetate in hexanes to yield [exo] 2-aza-2-benzylcarbonyl-6-((4-(propylthio)-1,2,5-thiadiazol-3-yl)oxy)bicyclo[2.2.1]heptane (0.8 g/2.0 mmol).

[exo] 2-Aza-2-benzylcarbonyl-6-((4-propylsulfonyl-1,2,5-thiadiazol-3-yl)oxy)bicyclo[2.2.1]heptane

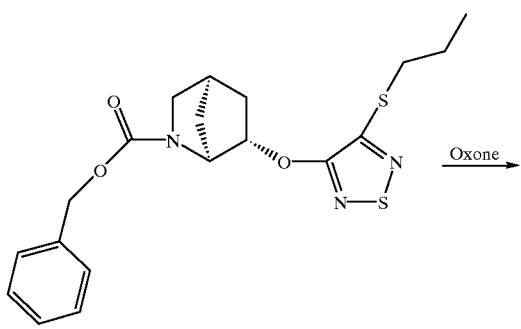

A solution of Oxone® (1.9 g/3.2 mmol) in water (10 mL) was added to a solution of [exo] 2-aza-2-benzylcarbonyl-6-((4-(propylthio)-1,2,5-thiadiazol-3-yl)oxy)bicyclo[2.2.1]heptane (0.8 g/2.0 mmol), water (4 mL), 1N HCl(aq) (2.9 ml), and tetrahydrofuran (20 mL). Stirred at room temperature for four hours. The reaction was poured into water then extracted with ethyl acetate. The organic extracts were dried over sodium sulfate, then evaporated to yield [exo] 2-aza-2-(benzylcarbonyl-6-((4-propylsulfonyl-1,2,5-thiadiazol-3-yl)oxy)bicyclo[2.2.1]heptane (0.7 g/1.6 mmol).

[exo] 2-Aza-6-((4-propylsulfonyl-1,2,5-thiadiazol-3-yl)oxy)bicyclo[2.2.1]heptane

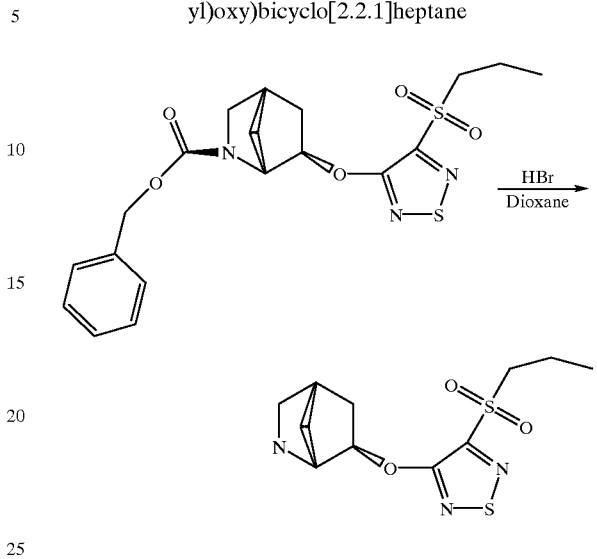

Hydrobromic acid was added (three minutes) above the surface of a solution of [exo] 2-aza-2-(benzylcarbonyl-6-((4-propylsulfonyl-1,2,5-thiadiazol-3-yl)oxy)bicyclo[2.2.1]heptane (2.2 mmol) in dioxane (50 mL). The reaction was stirred at room temperature for about two hours. The reaction was poured into ethyl acetate, the aqueous layer was basified with aqueous sodium hydroxide, then extracted with ethyl acetate. The combined organic extracts were dried over sodium sulfate then evaporated to yield [exo] 2-aza-6-((4-propylsulfonyl-1,2,5-thiadiazol-3-yl)oxy)bicyclo[2.2.1]heptane (0.57 mg/1.9 mmol).

[exo] 2-Aza-6-((4-cyclopropylethoxy-1,2,5-thiadiazol-3-yl)oxy)bicyclo[2.2.1]heptane

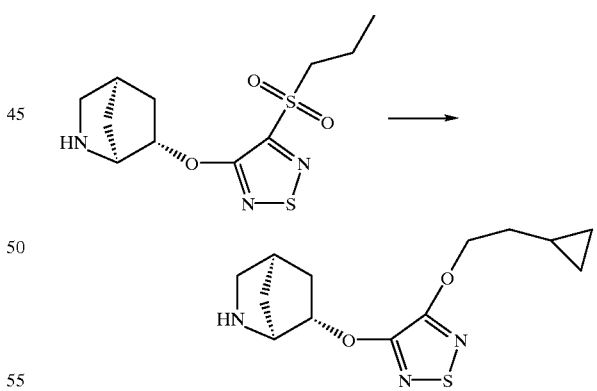

Potassium butoxide (6 mmol) was added to a solution of cyclopropylethanol (6 mmol) and tetrahydrofuran (70 mL) at 0_C. The reaction was stirred for 45 minutes at 0_C. [exo] 2-Aza-2-benzylcarbonyl-6-((4-propylsulfonyl-1,2,5-thiadiazol-3-yl)oxy)bicyclo[2.2.1]heptane (2.0 mmol) was added to the reaction. The reaction was stirred for 3 hours while warming to room temperature. The reaction was poured into ethyl acetate then washed with water. The extracts were basifed, dried over sodium sulfate then evaporated to yield [exo] 2-aza-6-((4-cyclopropylethoxy-1,2,5- thiadiazol-3-yl)oxy)bicyclo[2.2.1]heptane which was isolated as the maleate salt to yield 400 mg of LY344171 (mp=103–131__C.).

The following compounds were made by following substantially the same procedure described above, except that the corresponding starting materials were selected to provide the desired compounds.

[exo] 2-Aza-((4-(cyclopropylmethoxy)-1,2,5-thiadiazol-3-yl)oxy)bicyclo[2.2.1]heptane maleate, LY344180, mp 129–130__C.

[exo] 2-Aza-((4-(4-fluorobutoxy)-1,2,5-thiadiazol-3-yl)oxy)bicyclo[2.2.1]heptane maleate, LY344734, mp 136–139__C.

[exo] 2-Aza-((4-(4-fluorobenzyloxy)-1,2,5-thiadiazol-3-yl)oxy)bicyclo[2.2.1]heptane maleate, LY344735, mp 164–165__C.

[exo] 2-Aza-((4-((2-thienyl)methoxy)-1,2,5-thiadiazol-3-yl)oxy)bicyclo[2.2.1]heptane maleate, LY344736, mp 148–149__C.

[exo] 2-Aza-((4-(2-(2-thienyl)ethoxy))-1,2,5-thiadiazol-3-yl)oxy)bicyclo[2.2.1]heptane maleate, LY344737, mp 140–142__C.

Z, [exo] 2-Aza-((4-(2-butenyloxy))-1,2,5-thiadiazol-3-yl)oxy)bicyclo[2.2.1]heptane maleate, LY34739, mp 122–123__C.

[exo] 2-Aza-((4-(3-butenyloxy)-1,2,5-thiadiazol-3-yl)oxy)bicyclo[2.2.1]heptane hydrochloride, LY344740, mp 169–170__C.

[exo] 2-Aza-((4-(3-butynyloxy)-1,2,5-thiadiazol-3-yl)oxy)bicyclo[2.2.1]heptane hydrochloride, LY344876, mp 183–185__C.

[exo] 2-Aza-((4-(2-butenyloxy)-1,2,5-thiadiazol-3-yl)oxy)bicyclo[2.2.1]heptane hydrochloride, LY344740, mp 169–170__C.

E, [exo] 2-Aza-((4-(2-butenyloxy))-1,2,5-thiadiazol-3-yl)oxy)bicyclo[2.2.1]heptane hydrochloride, LY344877, mp 169–170__C.

[exo] 2-Aza-((4-(2-(3-thienyl)ethoxy))-1,2,5-thiadiazol-3-yl)oxy)bicyclo[2.2.1]heptane maleate, LY344878, mp 139–140__C.

[exo] 2-Aza-((4-(2-(4-fluorophenyl)ethoxy)-1,2,5-thiadiazol-3-yl)oxy)bicyclo[2.2.1]heptane hydrochloride, LY344883, mp 184–185__C.

[exo] 2-Aza-((4-(cyclobutylmethoxy)-1,2,5-thiadiazol-3-yl)oxy)bicyclo[2.2.1]heptane hydrochloride, LY344896, mp 166–167__C.

[exo] 2-Aza-((4-(2-(4-chlorophenyl)-2-cyclopropylethoxy)-1,2,5-thiadiazol-3-yl)oxy)bicyclo[2.2.1]heptane hydrochloride, LY344911, mp 119–120__C.

[exo] 2-Aza-((4-((methylcyclopropyl)methoxy)-1,2,5-thiadiazol-3-yl)oxy)bicyclo[2.2.1]heptane hydrochloride, LY344912 mp 155–156__C.

[exo] 2-Aza-((4-(2-propynyloxy)-1,2,5-thiadiazol-3-yl)oxy)bicyclo[2.2.1]heptane hydrochloride, LY344967, mp 158–160__C.

[exo] 2-Aza-((4-(4-(trifluoromethyl)benzyloxy)-1,2,5-thiadiazol-3-yl)oxy)bicyclo[2.2.1]heptane hydrochloride, LY344968, mp 180–183__C.

[exo] 2-Aza-((4-benzyloxy)-1,2,5-thiadiazol-3-yl)oxy)bicyclo[2.2.1]heptane hydrochloride, LY348066, mp 175–176__C.

[exo] 2-Aza-((4-(3-thienyl)methoxy)-1,2,5-thiadiazol-3-yl)oxy)bicyclo[2.2.1]heptane maleate, LY348630, mp 148–148.5__C.

[exo] 2-Aza-((4-(2-propenyloxy)-1,2,5-thiadiazol-3-yl)oxy)bicyclo[2.2.1]heptane maleate, LY349390, mp 129–131__C.

We claim:

1. A compound of formula I:

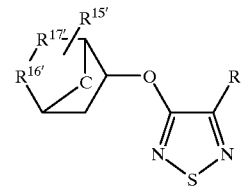

R is selected from the group consisting of —OR$^4$, —SR$^4$ and SO$_2$R$^4$;

R$^4$ is selected from the group consisting of C$_{1-15}$-alkyl, C$_{2-15}$-alkenyl, C$_{2-15}$-alkynyl, fused aromatic, and 5-membered heterocycle; each of which is optionally substituted with one or more independently selected from the group consisting of C$_3$–C$_8$ cycloalkyl, halogen, —CF$_3$, —CN, C$_{1-4}$ alkoxy, fused aromatic, 5-membered heterocycle, phenyl and phenoxy wherein phenyl, fused aromatic, and phenoxy is optionally substituted with one or more independently selected from the group consisting of halogen, —CN, C$_{1-4}$-alkyl, C$_{1-4}$-alkoxy, —OCF$_3$, —CF$_3$, —CONH$_2$ and —CSNH$_2$;

R$^{16'}$ is carbon or nitrogen;

R$^{17'}$ is carbon or nitrogen;

provided that one, and only one, of R$^{16'}$ and R$^{17'}$ must be nitrogen and when R$^{16'}$ is nitrogen then R$^{17'}$ is carbon and when R$^{17'}$ is nitrogen then R$^{16'}$ is carbon;

R$^{15'}$ is selected from the group consisting of hydrogen, C$_{1-4}$ alkyl, C$_{1-4}$ alkenyl, C$_{1-4}$ alkynyl, —C(O)OR$^{20'}$ and C$_3$–C$_8$ cycloalkyl;

R$^{20'}$ is C$_1$–C$_6$ alkyl; or a pharmaceutically acceptable salt or solvate thereof.

2. A compound of claim 1 wherein R is —OR$^4$.

3. A compound of claim 1 wherein R is —SR$^4$.

4. A compound of claim 1 wherein R$^{15'}$ is hydrogen.

5. A compound of claim 1 wherein R$^{16'}$ is nitrogen.

6. A compound of claim 1 wherein R$^{17'}$ is nitrogen.

7. A compound of claim 1 wherein the substitution is EXO.

8. A compound of claim 5 wherein R$^{15'}$ is at the R$^{16'}$ position.

9. A compound of claim 6 wherein R$^{15'}$ is at the R$^{17'}$ position.

10. A formulation comprising a compound of claim 1 associated with one or more carriers, diluents, or excipients therefor.

11. A method for modulating a muscarinic receptor comprising administering an effective amount of a compound of claim 1 to a patient in need thereof.

12. A method of claim 11 wherein the compound acts as a muscarinic receptor antagonist.

13. A method of claim 11 wherein the compound acts as a muscarinic receptor agonist.

14. A method for treating a condition associated with the malfunctioning of the muscarinic cholinergic system comprising administering an effective amount of a compound as claimed by claim 1 to a mammal in need thereof.

15. A method according to claim 14 wherein the condition associated with the malfunctioning of the muscarinic cholinergic system is selected from the group consisting of glaucoma, psychosis, schizophrenia, schizophreniform conditions, depression, sleeping disorders, epilepsy, Alzheimer's Disease, incontinence, and gastrointestinal motility disorders.

16. A method according to claim 15 wherein the condition associated with the malfunctioning of the muscarinic cholinergic system is selected from the group consisting of psychosis, schizophrenia, and schizophreniform conditions.

17. A method according to claim 15 wherein the condition associated with the malfunctioning of the muscarinic cholinergic system is Alzheimer's Disease.

18. A compound according to claim 1 selected from the group consisting of (1S,4R, 6S)-2-Aza-((4-cyclobutylmethoxy -1,2,5-thiadiazol-3-yl)oxy)bicyclo [2.2.1]heptane; (1S,4R, 6S)-2-Aza-((4-(2-cyclopropylethoxy)-1,2,5-thiadiazol-3-yl)oxy)bicyclo [2.2.1]heptane; (1S,4R, 6S)-2-Aza-((4-(diphenylmethoxy)-1,2,5-thiadiazol-3-yl)oxy)bicyclo[2.2.1]heptane; (1S,4R, 6S)-2-Aza-((4-propoxy-1,2,5-thiadiazol-3-yl)oxy)bicyclo [2.2.1]heptane; (1S,4R, 6S)-E-2-Aza-((4-(3-phenylprop-2-eneoxy)-1,2,5-thiadiazol-3-yl)oxy)bicyclo[2.2.1]heptane; (1S,4R, 6S)-2-Aza-((4-(3,3,3-trifluoropropoxy)-1,2,5-thiadiazol-3-yl)oxy)bicyclo[2.2.1]heptane; (1S,4R, 6S)-2-Aza-((4-cyclopentoxy-1,2,5-thiadiazol-3-yl)oxy)bicyclo [2.2.1]heptane; (1S,4R, 6S)-2-Aza-((4-cyclohexoxy-1,2,5-thiadiazol-3-yl)oxy)bicyclo[2.2.1]heptane; (1S,4R, 6S)-2-Aza-((4-(1-methylethoxy)-1,2,5-thiadiazol-3-yl)oxy)bicyclo[2.2.1]heptane;(1S,4R, 6S)-2-Aza-((4-(2-cyclopropylethoxy)-1,2,5-thiadiazol-3-yl)oxy)bicyclo [2.2.1]heptane; (1S,4R, 6S)-2-Aza-((4-(2-methylpropoxy)-1,2,5-thiadiazol-3-yl)oxy)bicyclo[2.2.1]heptane; (1S,4R, 6S)-2-Aza-((4-cyclobutoxy-1,2,5-thiadiazol-3-yl)oxy) bicyclo[2.2.1]heptane; 1S,4R, 6S)-2-Aza-((4-heptoxy-1,2,5-thiadiazol-3-yl)oxy)bicyclo[2.2.1]heptane; (1S,4R, 6S)-2-Aza-((4-(3-methylbutoxy)-1,2,5-thiadiazol-3-yl)oxy) bicyclo[2.2.1]heptane; (1S,4R, 6S)-2-Aza-((4-cyclohexylmethoxy-1,2,5-thiadiazol-3-yl)oxy)bicyclo [2.2.1]heptane; (1S,4R, 6S)-2-Aza-((4-cyclopentylmethoxy-1,2,5-thiadiazol-3-yl)oxy)bicyclo[2.2.1]heptane; (1S,4R, 6S)-2-Aza-((4-(2 -cyclohexylethoxy)-1,2,5-thiadiazol-3-yl) oxy)bicyclo[2.2.1]heptane; (1S,4R, 6S)-2-Aza-((4-(2-oxetane-2-methylethoxy)-1,2,5-thiadiazol-3-yl)oxy)bicyclo [2.2.1]heptane; (1S,4R, 6S)-2-Aza-((4-cycloheptylmethoxy-1,2,5-thiadiazol-3-yl)oxy)bicyclo[2.2.1]heptane; (1R,4S, 6R)-2-Aza-((4-cyclobutylmethoxy-1,2,5-thiadiazol-3-yl) oxy)bicyclo[2.2.1]heptane; (1R,4S,6R)-2-Aza-((4-(2-cyclopropylethoxy)-1,2,5-thiadiazol-3yl)oxy)bicyclo[2.2.1] heptane; (1R,4S,6R)-2-Aza-((4-propoxy)-1,2,5-thiadiazol-3-yl)oxy)bicyclo[2.2.1]heptane; (1R,4S,6R,1'R,4'S,6'R)-3,4-Di-((2-azabicyclo[2.2.1]heptan-6-yl)oxy)-1,2,5-thiadiazole; (1S,4R, 6S)-2-Aza-((4-(4-chlorophenylmethylthio)-1,2,5-thiadiazol-3-yl)oxy)bicyclo [2.2.1]heptane; (1S,4R, 6S)-2-Aza-((4-cyclobutylmethylthio-1,2,5-thiadiazol-3-yl)oxy)bicyclo [2.2.1]heptane; (1S,4R, 6S)-2-Aza-((4-(4fluorophenylmethylthio)-1,2,5-thiadiazol-3-yl)oxy) bicyclo[2.2.1]heptane; (1S,4R, 6S)-2-Aza-((4-(2-cyclopropylethylthio)-1,2,5-thiadiazol-3-yl)oxy)bicyclo [2.2.1]heptane; (1S,4R,6S)-2-Aza-((4-(2-thienylthio)-1,2,5-thiadiazol-3-yl)oxy)bicyclo[2.2.1]heptane; [exo]2-Aza-5-((4-propylthio-1,2,5-thiadiazol-3-yl)oxy)bicyclo[2.2.1] heptane; [exo]-2-aza-5-((4-hexoxy-1,2,5-thiadiazol-3-yl) oxy)bicyclo[2.2.1]heptane; [exo]-2-aza-5-((4-(2-methylpropoxy)-1,2,5-thiadiazol-3-yl)oxy)bicyclo[2.2.1] heptane; [exo]-2-aza-5-((4-(4-fluorophenylmethoxy)-1,2,5-thiadiazol-3-yl)oxy)bicyclo[2.2.1]heptane; [endo]-2-Aza-((4-cyclobutylmethoxy-1,2,5-thiadiazol-3-yl)oxy)bicyclo [2.2.1]heptane; [endo]-2-aza-6-((4-(4-fluorophenylmethoxy)-1,2,5-thiadiazol-3-yl)oxy)bicyclo [2.2.1]heptane; [exo]2-Aza-5-((4-propylsulfonyl-1,2,5-thiadiazol-3-yl)oxy)bicyclo[2.2.1]heptane; [exo]2-Aza-5-((4-(2-cyclopropylethoxy)-1,2,5-thiadiazol-3-yl)oxy) bicyclo[2.2.1]heptane; (1S,4R, 6S)-2-Aza-((4-(2-thienylthio)-1,2,5-thiadiazol-3-yl)oxy)bicyclo[2.2.1] heptane yl)oxy)bicyclo[2.2.1]heptane; (1R,4S,6R)-2-Aza-((4-(4-fluorophenylthio)-1,2,5-thiadiazol-3-yl)oxy)bicyclo [2.2.1]heptane; [endo] 2-Aza-2-(t-butoxycarbonyl)-5-((4-propylthio-1,2,5-thiadiazol-3-yl)oxy)bicyclo [2.2.1] heptane; [endo] 2-Aza-6-((4-propylthio-1,2,5-thiadiazol-3-yl)oxy)bicyclo[2.2.1]heptane; [exo] 2-Aza-6-((4-(4,4,4-trifluorobutoxy)-1,2,5-thiadiazol-3-yl)oxy)bicyclo[2.2.1] heptane; [exo] 2-Aza-6-((4-(4-(trifluoromethoxy) benzyloxy)-1,2,5-thiadiazol-3-yl)oxy)bicyclo[2.2.1] heptane; [exo] 2-Aza-6-((4-propoxy-1,2,5-thiadiazol-3-yl) oxy)bicyclo[2.2.1]heptane; [exo] 2-Aza-6-((4-ethyloxy-1,2,5-thiadiazol-3-yl)oxy)bicyclo[2.2.1]heptane; [exo] 2-Aza-6-(4-hexoxy-1,2,5-thiadiazol-3-yloxy)bicyclo[2.2.1]heptane; [exo] 2-Aza-6-((4-propylsulfonyl-1,2,5-thiadiazol-3-yl) oxy)bicyclo[2.2.1]heptane; [exo] 2-Aza-6-((4-methoxy-1,2,5-thiadiazol-3-yl)oxy)bicyclo[2.2.1]heptane; [exo] 2-Aza-6-((4-(ethylthio)-1,2,5-thiadiazol-3-yl)oxy)bicyclo[2.2.1] heptane; [exo] 2-Aza-6-((4-butoxy-1,2,5-thiadiazol-3-yl) oxy)bicyclo[2.2.1]heptane; [exo] 2-Aza-6-((4-hexoxy-1,2,5-thiadiazol-3-yl)oxy)bicyclo[2.2.1]heptane; (1R,4S,6R)-2-Aza-((4-(2-(4-chlorophenyl)-2-cyclopentylethoxy)-1,2,5-thiadiazol-3-yl)oxy)bicyclo[2.2.1]heptane; (1R,4S,6R)-2-Aza-((4-(4-chlorobenzyl)thio)-1,2,5-thiadiazol-3-yl)oxy) bicyclo[2.2.1]heptane; (1R,4S,6R)-2-Aza-((4-(3-(4-fluorophenyl)propoxy)-1,2,5-thiadiazol-3-yl)oxy)bicyclo [2.2.1]heptane; (1R,4S,6R)-2-Aza-((4-(3-phenyl)prop-2-ynyloxy)-1,2,5-thiadiazol-3-yl)oxy)bicyclo[2.2.1]heptane; (1R,4S,6R)-2-Aza-((4-(hexyloxy-1,2,5-thiadiazol-3-yl)oxy) bicyclo[2.2.1]heptane; (1R,4S,6R)-2-Aza-((4-but-2-ynyloxy-1,2,5-thiadiazol-3 -yl)oxy)bicyclo[2.2.1]heptane; (1R,4S,6R)-2-Aza-((4-(2-cyclproylethoxy)-1,2,5-thiadiazol-3-yl)oxy)bicyclo[2.2.1]heptane; (1R,4S,6R)-2-Aza-((4-(4-fluorobenzyl)thio)-1,2,5-thiadiazol-3-yl)oxy) bicyclo[2.2.1]heptane; (1S,4R,6S)-2-Aza-((4-(2-cyclohexyl-cyclohexoxy)-1,2,5-thiadiazol-3-yl)oxy)bicyclo [2.2.1]heptane; (1S,4R,6S)-2-Aza-((4-(4-phenylbenzyloxy)-1,2,5-thiadiazol-3-yl)oxy)bicyclo[2.2.1] heptane; (1S,4R,6S)-2-Aza-((4-(2-(4-chlorophenylthio) ethyoxy)-1,2,5-thiadiazol-3-yl)oxy)bicyclo[2.2.1]heptane; (1S,4R,6S)-2-Aza-((4-(2-phenyl-2-cyclopropylethoxy)-1,2,5-thiadiazol-3-yl)oxy)bicyclo[2.2.1]heptane; (1S,4R,6S)-2-Aza-((4-(3-(benzyloxy)propoxy)-1,2,5-thiadiazol-3-yl)oxy) bicyclo[2.2.1]heptane; (1S,4R,6S)-2-Aza-((4-(2-diphenyethoxy)-1,2,5-thiadiazol-3-yl)oxy)bicyclo[2.2.1] heptane; (1S,4R,6S)-2-Aza-((4-(1-(2-thienyl)-2-propoxy)-1,2,5-thiadiazol-3-yl)oxy)bicyclo[2.2.1]heptane; (1S,4R,6S)-2-Aza-((4-(2-phenyl-2-cyclopentylethoxy)-1,2,5-thiadiazol-3-yl)oxy)bicyclo[2.2.1]heptane; (1S,4R,6S)-2-Aza-((4-(3-(methylthio)-1-hexoxy)-1,2,5-thiadiazol-3-yl)oxy)bicyclo [2.2.1]heptane; (1S,4R,6S)-2-Aza-((4-(2,3-pentafluoro-1-propoxy)-1,2,5-thiadiazol-3-yl)oxy)bicyclo[2.2.1]heptane; [exo] 2-Aza-6-((4-propylsulfonyl-1,2,5-thiadiazol-3-yl) oxy)bicyclo[2.2.1]heptane; [endo]2-Aza-5-((4-propylthio-1,2,5-thiadiazol-3-yl)oxy)bicyclo[2.2.1]heptane; [exo] 2-Aza-2-benzyl-6-((4-butoxy-1,2,5-thiadiazol-3-yl)oxy)bicyclo [2.2.1]heptane; [exo] 2-Aza-6-((4-cyclopropylethoxy-1,2,5-thiadiazol-3-yl)oxy)bicyclo[2.2.1]heptane; [exo] 2-Aza-((4-(cyclopropylmethoxy)-1,2,5-thiadiazol-3-yl) oxy)bicyclo [2.2.1]heptane; [exo] 2-Aza-((4-(4 -fluorobutoxy)-1,2,5- thiadiazol-3-yl)oxy)bicyclo[2.2.1]heptane; [exo] 2-Aza-((4-(4-fluorobenzyloxy)-1,2,5-thiadiazol-3-yl)oxy)bicyclo[2.2.1]heptane; [exo] 2-Aza-((4-((2-thienyl)methoxy)-1,2,5-thiadiazol-3-yl)oxy)bicyclo[2.2.1]heptane; [exo] 2-Aza-((4-(2-(2-thienyl)ethoxy))-1,2,5-thiadiazol-3-yl)oxy)bicyclo[2.2.1]heptane; Z-[exo] 2-Aza-((4-(2-butenyloxy))-1,2,5-thiadiazol-3-yl)oxy)bicyclo[2.2.1]heptane; [exo] 2-Aza-((4-(3-butenyloxy)-1,2,5-thiadiazol-3-yl)oxy)bicyclo[2.2.1]heptane; [exo] 2-Aza-((4-(3-butynyloxy)-1,2,5-thiadiazol-3-yl)oxy)bicyclo[2.2.1]heptane; [exo] 2-Aza-((4-(2-butenyloxy)-1,2,5-thiadiazol-3-yl)oxy)bicyclo[2.2.1]heptane E-[exo] 2-Aza-((4-(2-butenyloxy))-1,2,5-thiadiazol-3-yl)oxy)bicyclo[2.2.1]heptane; [exo] 2-Aza-((4-(2-(3-thienyl)ethoxy))-1,2,5-thiadiazol-3-yl)oxy)bicyclo[2.2.1]heptane; [exo] 2-Aza-((4-(2-(4-fluorophenyl)ethoxy)-1,2,5-thiadiazol-3-yl)oxy)bicyclo[2.2.1]heptane; [exo] 2-Aza-((4-(cyclobutylmethoxy)-1,2,5-thiadiazol-3-yl)oxy)bicyclo[2.2.1]heptane; [exo] 2-Aza-((4-(2-(4-chlorophenyl)-2-cyclopropylethoxy)-1,2,5-thiadiazol-3-yl)oxy)bicyclo[2.2.1]heptane; [exo] 2-Aza-((4-((methylcyclopropyl)methoxy)-1,2,5-thiadiazol-3-yl)oxy)bicyclo[2.2.1]heptane; [exo] 2-Aza-((4-(2-propynyloxy)-1,2,5-thiadiazol-3-yl)oxy)bicyclo[2.2.1]heptane; [exo] 2-Aza-((4-(4-(trifluoromethyl)benzyloxy)-1,2,5-thiadiazol-3-yl)oxy)bicyclo[2.2.1]heptane; [exo] 2-Aza-((4-benzyloxy)-1,2,5-thiadiazol-3-yl)oxy)bicyclo[2.2.1]heptane; [exo] 2-Aza-((4-(3-thienyl)methoxy)-1,2,5-thiadiazol-3-yl)oxy)bicyclo[2.2.1]heptane; [exo] 2-Aza-6-((4-propyl thio-1,2,5-thiadiazol-3-yl)oxy)bicyclo[2.2.1]heptane; [exo] 2-Aza-5-((4-propyl thio-1,2,5-thiadiazol-3-yl)oxy)bicyclo[2.2.1]heptane; [exo] 2-Aza-6-((4-butoxy-1,2,5-thiadiazol-3-yl)oxy)bicyclo[2.2.1]heptane; [exo] 2-Aza-5-((4 -butoxy-1,2,5-thiadiazol-3-yl)oxy)bicyclo[2.2.1]heptane; [exo] 2-Aza-5-((4-propoxy-1,2,5-thiadiazol-3-yl)oxy)bicyclo[2.2.1]heptane; and [exo] 2-Aza-((4-(2-propenyloxy)-1,2,5-thiadiazol-3-yl)oxy)bicyclo[2.2.1]heptane.

19. A compound according to claim 18 wherein the compound is as its hydrochloride salt.

20. A compound according to claim 1 selected from the group consisting of (1S,4R, 6S)-2-Aza-2-(t-butoxycarbonyl)-6-((4-(propylthio)-1,2,5-thiadiazol-3-yl)oxy)bicyclo[2.2.1]heptane; (1S,4R, 6S)-2-Aza-2-(t-butoxycarbonyl)-6-((4-propylsulfonyl-1,2,5-thiadiazol-3-yl)oxy)bicyclo[2.2.1]heptane; (1S,4R, 6S)-2-Aza-2-(t-butoxycarbonyl)-6-((4-cyclobutylmethoxy-1,2,5-thiadiazol-3-yl)oxy)bicyclo[2.2.1]heptane; (1S,4R, 6S)-2-Aza-2-(t-butoxycarbonyl)-6-((4-(4-chlorophenylmethylthio)-1,2,5-thiadiazol-3-yl)oxy)bicyclo[2.2.1]heptane; (1S,4R, 6S)-2-Aza-2-(t-butoxycarbonyl)-((4-(2-thienylthio)-1,2,5-thiadiazol-3-yl)oxy)bicyclo[2.2.1]heptane; [exo] 2-Aza-2-(t-butoxycarbonyl)-5-((4-propylthio-1,2,5-thiadiazol-3-yl)oxy)bicyclo[2.2.1]heptane; [exo] 2-Aza-2-(t-butoxycarbonyl)-5-((4-propylthio-1,2,5-thiadiazol-3-yl)oxy)bicyclo[2.2.1]heptane; [exo] 2-Aza-2-(t-butoxycarbonyl)-5-((4-propylsulfonyl-1,2,5-thiadiazol-3-yl)oxy)bicyclo[2.2.1]heptane; [exo]2-Aza-2-(t-butoxycarbonyl)-5-((4-cyclobutylmethylthio-1,2,5-thiadiazol-3-yl)oxy)bicyclo[2.2.1]heptane; [endo]-2-Aza-2-(t-butoxycarbonyl)-6-((4-(propylthio)-1,2,5-thiadiazol-3-yl)oxy)bicyclo[2.2.1]heptane; [endo]-2-Aza-2-(t-butoxycarbonyl)-6-((4-propylsulfonyl-1,2,5-thiadiazol-3-yl)oxy)bicyclo[2.2.1]heptane; [endo]-2-Aza-2-(t-butoxycarbonyl)-6-((4-cyclobutylmethoxy-1,2,5-thiadiazol-3-yl)oxy)bicyclo[2.2.1]heptane; [exo] 2-Aza-2-benzyl-6-((4-propylsulfonyl-1,2,5-thiadiazol-3-yl)oxy)bicyclo[2.2.1]heptane; [exo] 2-Aza-2-benzyl-6-((4 -(4,4,4-trifluorobutoxy)-1,2,5-thiadiazol-3-yl)oxy)bicyclo[2.2.1]heptane; [exo] 2-Aza-2-t-butoxycarbonyl)-6-((4-propylthio-1,2,5-thiadiazol-3-yl)oxy)bicyclo[2.2.1]heptane; [exo] 2-Aza-2-(methoxycarbonyl)-6-((4-(ethylthio)-1,2,5-thiadiazol-3-yl)oxy)bicyclo[2.2.1]heptane; [exo] 2-Aza-2-benzyl-6-((4-propyl thio-1,2,5-thiadiazol-3-yl)oxy)bicyclo[2.2.1]heptane; [endo] 2-Aza-2-benzyl-6-((4-propylthio-1,2,5-thiadiazol-3-yl)oxy)bicyclo[2.2.1]heptane; [exo] 2-Aza-2-benzylcarbonyl-6-((4-(propylthio)-1,2,5-thiadiazol-3-yl)oxy)bicyclo[2.2.1]heptane; and [exo] 2-Aza-2-benzylcarbonyl-6-((4-propylsulfonyl-1,2,5-thiadiazol-3-yl)oxy)bicyclo[2.2.1]heptane.

* * * * *